(12) United States Patent
Jung et al.

(10) Patent No.: US 10,131,662 B2
(45) Date of Patent: Nov. 20, 2018

(54) PESTICIDALLY ACTIVE TETRACYCLIC DERIVATIVES WITH SULFUR CONTAINING SUBSTITUENTS

(71) Applicant: Syngenta Participations AG, Basel (CH)

(72) Inventors: Pierre Joseph Marcel Jung, Stein (CH); Andrew Edmunds, Stein (CH); Michel Muehlebach, Stein (CH); Roger Graham Hall, Stein (CH); Jerome Yves Cassayre, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/554,297

(22) PCT Filed: Mar. 7, 2016

(86) PCT No.: PCT/EP2016/054758
§ 371 (c)(1),
(2) Date: Aug. 29, 2017

(87) PCT Pub. No.: WO2016/142327
PCT Pub. Date: Sep. 15, 2016

(65) Prior Publication Data
US 2018/0079748 A1    Mar. 22, 2018

(30) Foreign Application Priority Data

Mar. 12, 2015 (EP) ..................................... 15158770

(51) Int. Cl.
| | | |
|---|---|---|
| *C07D 401/14* | (2006.01) | |
| *A61K 31/437* | (2006.01) | |
| *A61K 31/4353* | (2006.01) | |
| *C07D 471/04* | (2006.01) | |
| *C07D 409/04* | (2006.01) | |
| *C07D 487/04* | (2006.01) | |
| *A01N 43/52* | (2006.01) | |
| *A01N 43/90* | (2006.01) | |

(52) U.S. Cl.
CPC ........... *C07D 471/04* (2013.01); *A01N 43/52* (2013.01); *A01N 43/90* (2013.01); *C07D 409/04* (2013.01); *C07D 487/04* (2013.01)

(58) Field of Classification Search
CPC .. C07D 401/02; C07D 401/10; C07D 401/14; A61K 31/437; A61K 31/4353
USPC .......................... 514/300, 303; 546/119, 121
See application file for complete search history.

(56) References Cited

U.S. PATENT DOCUMENTS 7,105,505 B2 *   9/2006   Zeng ................... C07D 401/14
                                                  514/210.21

FOREIGN PATENT DOCUMENTS

| WO | 2012/086848 A1 | 6/2012 |
|---|---|---|
| WO | 2013/018928 A1 | 2/2013 |

OTHER PUBLICATIONS

Extended European Search Report for No. 15158770.6 dated May 27, 2015.
International Search Report and Written Opinion for PCT/EP2016/054758, dated Apr. 15, 2016.

* cited by examiner

*Primary Examiner* — Niloofar Rahmani
(74) *Attorney, Agent, or Firm* — Dinsmore & Shohl LLP; Toni-Junell Herbert

(57) ABSTRACT

Compounds of formula (I), wherein the substituents are as defined in claim 1, and the agrochemically acceptable salts, stereoisomers, enantiomers, tautomers and N-oxides of those compounds, can be used as insecticides and can be prepared in a manner known per se.

12 Claims, No Drawings ns # PESTICIDALLY ACTIVE TETRACYCLIC DERIVATIVES WITH SULFUR CONTAINING SUBSTITUENTS

RELATED APPLICATION INFORMATION

This application is a 371 of International Application No. PCT/EP2016/054758, filed 7 Mar. 2016, which claims priority to EP Patent Application No. 15 158770.6, filed 12 Mar. 2015, the contents of which are incorporated herein by reference herein.

The present invention relates to pesticidally active, in particular insecticidally active tetracyclic derivatives containing sulfur substituents, to compositions comprising those compounds, and to their use for controlling animal pests (including arthropods and in particular insects or representatives of the order Acarina).

Heterocyclic compounds with pesticidal action are known and described, for example, in WO 2012/086848 and WO 2013/018928.

There have now been found novel pesticidally active tetracyclic derivatives with a sulfur containing bicyclic moiety.

The present invention accordingly relates to compounds of formula I, wherein
$A_1$ represents S, O or NCH$_3$;
$A_2$, $A_3$, $A_4$ and $A_5$, independently from each other, represent CR$_3$ or N;
X is S, SO or SO$_2$;
$R_1$ is $C_1$-$C_6$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano and $C_1$-$C_4$alkyl; or is $C_3$-$C_6$cycloalkyl-$C_1$-$C_4$alkyl mono- or polysubstituted by substituents selected from the group consisting of halogen, cyano and $C_1$-$C_4$alkyl;
$R_2$ is hydrogen, halogen, $C_1$-$C_4$haloalkylsulfanyl, $C_1$-$C_4$haloalkylsulfinyl, $C_1$-$C_4$haloalkylsulfonyl, O($C_1$-$C_4$haloalkyl), —SF$_5$, —C(O)$C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$haloalkyl and $C_1$-$C_4$alkyl;
$R_3$ is hydrogen, halogen, cyano, nitro, —SF$_5$, hydroxyl, amino, —NR$_9$R$_{10}$, C(O)NR$_9$R$_{10}$, $C_1$-$C_6$haloalkyl, $C_1$-$C_6$alkyl, $C_2$-$C_6$alkenyl, $C_2$-$C_6$alkynyl, $C_2$-$C_6$haloalkenyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, O($C_1$-$C_4$haloalkyl), —C(O)$C_1$-$C_4$haloalkyl, $C_1$-$C_6$haloalkoxy, $C_1$-$C_6$alkoxy, $C_2$-$C_4$alkylcarbonyl, $C_2$-$C_6$alkoxycarbonyl, or is $C_3$-$C_6$cycloalkyl which can be mono- or polysubstituted by R$_7$, or $C_3$-$C_6$cycloalkyl-$C_1$-$C_4$alkyl which can be mono- or polysubstituted by R$_8$;
$R_3$ is pyrazolyl which can be mono- or polysubstituted by halogen, cyano or $C_1$-$C_6$haloalkyl
$G_1$ is N or CR$_4$;
$G_2$ is N or CR$_5$;
$G_3$ is NR$_6$;
$R_6$ is $C_1$-$C_4$alkyl which can be mono- or polysubstituted by substituents selected from the group consisting of halogen and $C_1$-$C_2$alkylsulfinyl;
$R_4$ and $R_5$, independently from each other, are hydrogen, halogen, cyano, nitro, $C_1$-$C_6$alkyl, $C_1$-$C_6$haloalkyl, or are $C_3$-$C_6$cycloalkyl which can be mono- or polysubstituted by R$_7$; or are $C_3$-$C_6$cycloalkyl-$C_1$-$C_4$alkyl which can be mono- or polysubstituted by R$_8$; or
$R_4$ and $R_5$, independently from each other, are $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl $C_1$-$C_6$haloalkylsulfanyl, $C_1$-$C_4$haloalkylsulfonyl, $C_1$-$C_6$haloalkylsulfinyl or hydroxyl;
$R_7$ and $R_8$, independently from each other, are halogen, nitro, cyano, $C_1$-$C_4$haloalkoxy, $C_1$-$C_4$alkoxy $C_4$alkyl, $C_1$-$C_4$alkoxy, $C_1$-$C_4$alkyl or $C_1$-$C_4$haloalkyl; and
$R_9$ and $R_{10}$, independently from each other, are hydrogen, cyano, $C_1$-$C_3$ alkoxy or $C_1$-$C_6$alkyl; and agrochemically acceptable salts, stereoisomers, enantiomers, tautomers and N-oxides of those compounds.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

Preferably $R_1$ is $C_1$-$C_6$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano and $C_1$-$C_4$alkyl; or is $C_3$-$C_6$cycloalkyl-$C_1$-$C_4$alkyl mono- or polysubstituted by substituents selected from the group consisting of halogen, cyano and $C_1$-$C_4$alkyl;

$R_3$ is hydrogen, halogen, cyano, nitro, —$SF_5$, hydroxyl, amino, —$NR_9R_{10}$, $C(O)NR_9R_{10}$, $C_1$-$C_6$haloalkyl, $C_1$-$C_6$alkyl, $C_2$-$C_6$alkenyl, $C_2$-$C_6$alkynyl, $C_2$-$C_6$haloalkenyl, $C_2$-$C_6$haloalkynyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl, $O(C_1$-$C_4$haloalkyl), —$C(O)C_1$-$C_4$haloalkyl, $C_1$-$C_6$haloalkoxy, $C_1$-$C_6$alkoxy, $C_2$-$C_4$alkylcarbonyl, $C_2$-$C_6$alkoxycarbonyl, or is $C_3$-$C_6$cycloalkyl which can be mono- or polysubstituted by $R_7$, or $C_3$-$C_6$cycloalkyl-$C_1$-$C_4$alkyl which can be mono- or polysubstituted by $R_8$; and $R_7$ and $R_8$, independently from each other, are halogen, nitro, cyano, $C_1$-$C_4$haloalkoxy, $C_1$-$C_4$alkoxy $C_1$-$C_4$alkyl or $C_1$-$C_4$haloalkyl.

A preferred group of compounds of formula I is represented by the compounds of formula I-1

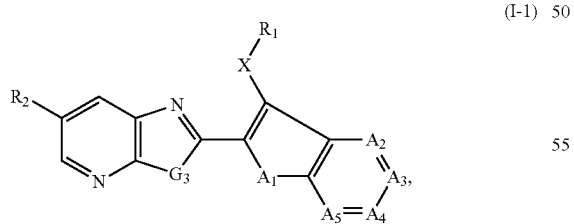

(I-1)

wherein the substituents X, $R_1$, $R_2$, $G_3$, $A_1$, $A_2$, $A_3$, $A_4$ and $A_5$ are as defined under formula I above.

Further preferred embodiments of the invention are:

EMBODIMENT (A1)

Preferred are compounds of formula I-1, wherein $A_1$ represents S, O or $NCH_3$;

$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl; and X, $G_3$, $A_2$, $A_3$, $A_4$ and $A_5$ are as defined under formula I above.

EMBODIMENT (A2)

Further preferred are compounds of formula I-1a

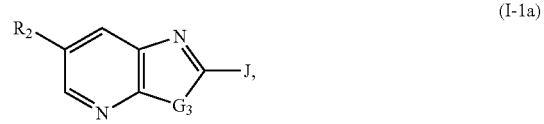

(I-1a)

wherein J is selected from the group consisting of

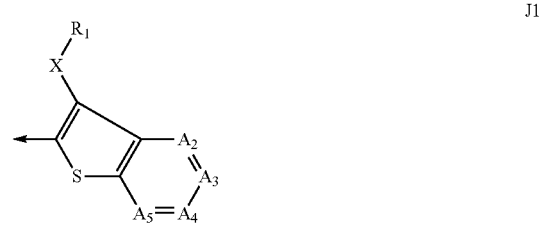

J1

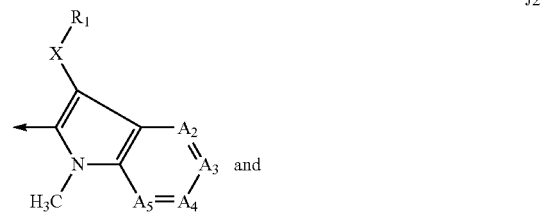

J2 and

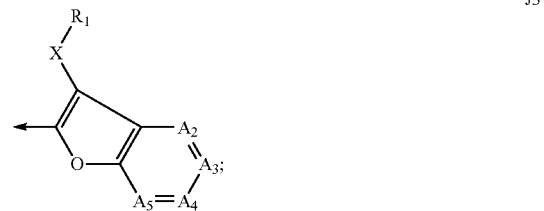

J3 wherein $G_3$, $R_1$, $R_2$, X, $A_2$, $A_3$, $A_4$ and $A_5$ are as defined under Embodiment (A1) above.

EMBODIMENT (A3)

Further preferred are compounds of formula I-1a

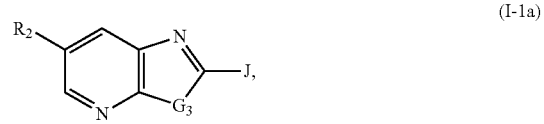

(I-1a)

wherein J is as defined under Embodiment (A2) above;
R$_1$ is C$_1$-C$_4$alkyl, C$_3$-C$_6$cycloalkyl-C$_1$-C$_4$alkyl or C$_3$-C$_6$cycloalkyl;
R$_2$ is halogen, C$_1$-C$_4$haloalkylsulfanyl, C$_1$-C$_4$haloalkylsulfinyl, C$_1$-C$_4$haloalkylsulfonyl, C$_1$-C$_4$haloalkoxy, C$_1$-C$_4$haloalkyl, cyano or C$_3$-C$_6$cycloalkyl;
X and G$_3$ is as defined under formula I above;
A$_2$, A$_3$, A$_4$ and A$_5$, independently from each other, represents CR$_3$ or N; and
R$_3$ is hydrogen, halogen, nitro, cyano, hydroxyl, C$_1$-C$_6$alkyl, C$_2$-C$_6$alkenyl, C$_2$-C$_6$alkynyl, C$_3$-C$_6$cycloalkyl, C$_3$-C$_6$cycloalkyl-C$_1$-C$_4$cycloalkyl, C$_1$-C$_6$haloalkyl, C$_2$-C$_6$haloalkenyl, C$_2$-C$_6$haloalkynyl, C$_3$-C$_6$halocycloalkyl, C$_3$-C$_6$cyclohaloalkyl-C$_1$-C$_4$cycloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

EMBODIMENT (A4)

Further preferred are compounds of formula I-1a

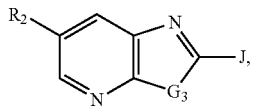
(I-1a)

wherein J is as defined under Embodiment (A2) above;
R$_1$ is C$_1$-C$_4$alkyl;
R$_2$ is C$_1$-C$_4$haloalkylsulfanyl, C$_1$-C$_4$haloalkylsulfinyl, C$_1$-C$_4$haloalkylsulfonyl, C$_1$-C$_4$haloalkoxy or C$_1$-C$_4$haloalkyl;
X is as defined under formula I above;
G$_3$ is N—R$_6$, wherein R$_6$ is as defined under formula I above;
A$_2$, A$_3$, A$_4$ and A$_5$, independently from each other, represents CR$_3$ or N; and
R$_3$ is hydrogen, halogen, nitro, cyano, hydroxyl, C$_1$-C$_6$alkyl, C$_2$-C$_6$alkenyl, C$_2$-C$_6$alkynyl C$_3$-C$_6$cycloalkyl, C$_3$-C$_6$cycloalkyl-C$_1$-C$_4$cycloalkyl, C$_1$-C$_6$haloalkyl, C$_2$-C$_6$haloalkenyl, C$_2$-C$_6$haloalkynyl, C$_3$-C$_6$halocycloalkyl, C$_3$-C$_6$cyclohaloalkyl-C$_1$-C$_4$cycloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

EMBODIMENT (A5)

Further preferred are compounds of formula I-1a

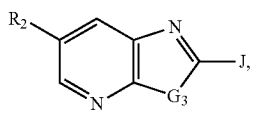
(I-1a)

wherein J is as defined under Embodiment (A2) above;
R$_1$ is C$_1$-C$_4$ alkyl;
R$_2$ is —OCF$_3$, —SCF$_3$, —S(O)CF$_3$, —S(O)$_2$CF$_3$ or CF$_3$;
X is as defined under formula I above;
G$_3$ is N—R$_6$, wherein R$_6$ is as defined under formula I above;
A$_2$, A$_3$, A$_4$ and A$_5$, independently from each other, represents CR$_3$ or N; and
R$_3$ is hydrogen, halogen, cyano, C$_1$-C$_6$alkyl, C$_2$-C$_6$alkenyl, C$_2$-C$_6$alkynyl, C$_1$-C$_6$haloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

EMBODIMENT (A6)

Further preferred are compounds of formula I-1a

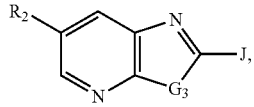
(I-1a)

wherein J is as defined under Embodiment (A2) above;
R$_1$ is ethyl;
R$_2$ is CF$_3$;
X is as defined under formula I above;
G$_3$ is N—R$_6$, wherein R$_6$ is as defined under formula I above;
A$_2$, A$_3$, A$_4$ and A$_5$, independently from each other, represents CR$_3$ or N; and
R$_3$ is hydrogen, bromo, chloro, iodo, fluoro, cyano, methyl, ethyl, isopropyl, propyl, trifluoromethyl, CF$_3$CH$_2$—, CH$_3$O, —SCF$_3$, —S(O)CF$_3$ or —S(O)$_2$CF$_3$.

EMBODIMENT (A7)

Further preferred are compounds of formula I-1a

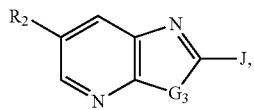
(I-1a)

wherein J is as defined under Embodiment (A2) above;
R$_1$ is ethyl;
R$_2$ is CF$_3$;
X is as defined under formula I above;
G$_3$ is N—R$_6$, wherein R$_6$ is as defined under formula I above;
A$_2$, A$_3$, A$_4$ and A$_5$, independently from each other, represents CR$_3$ or N; and
R$_3$ is hydrogen, bromo, chloro, iodo, fluoro, cyano, methyl, or trifluoromethyl.

EMBODIMENT (A8)

Further preferred are compounds of formula I-1a

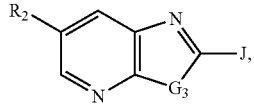
(I-1a)

wherein J is as defined under Embodiment (A2) above;
R$_1$ is ethyl;

$R_2$ is $CF_3$;
X is as defined under formula I above;
$G_3$ is N—$R_6$, $R_6$ is as defined under formula I above;
$A_2$, $A_3$, $A_4$ and $A_5$, independently from each other, represents $CR_3$ or N; and
$R_3$ is hydrogen in all groups J.

In all of the preferred embodiments of formula I-1 above, X is preferably S or $SO_2$ and $R_6$ is preferably methyl.

A preferred group of compounds of formula I is represented by the compounds of formula I-2

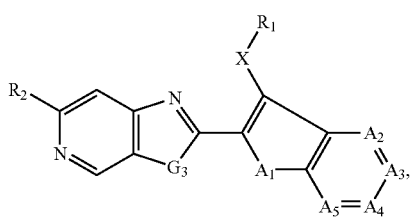

(I-2)

wherein the substituents X, A, $R_1$, $R_2$, $G_3$, $A_1$, $A_2$, $A_3$, $A_4$ and $A_5$ are as defined under formula I above.

EMBODIMENT (B1)

Preferred are compounds of formula I-2, wherein
$A_1$ represents S, O or $NCH_3$;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl; and
X, $G_3$, $A_2$, $A_3$, $A_4$ and $A_5$ are as defined under formula I above.

EMBODIMENT (B2)

Further preferred are compounds of formula I-2a

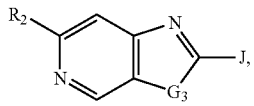

(I-2a)

wherein J is selected from the group consisting of

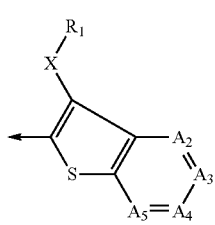

J1

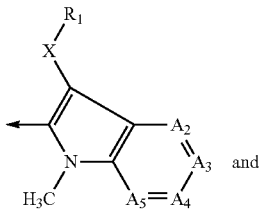

J2 and

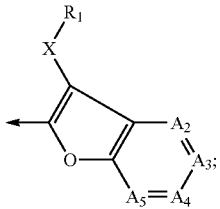

J3 wherein $G_3$, $R_1$, $R_2$, X, $A_2$, $A_3$, $A_4$ and $A_5$ are as defined under Embodiment (B1) above.

EMBODIMENT (B3)

Further preferred are compounds of formula I-2a

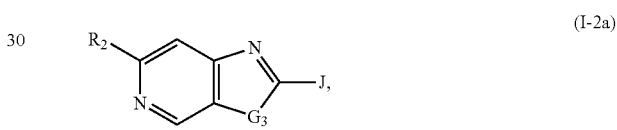

(I-2a)

wherein J is as defined under Embodiment (B2) above;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or $C_3$-$C_6$cycloalkyl;
X and $G_3$ is as defined under formula I above;
$A_2$, $A_3$, $A_4$ and $A_5$, independently from each other, represents $CR_3$ or N; and
$R_3$ is hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (B4)

Further preferred are compounds of formula I-2a

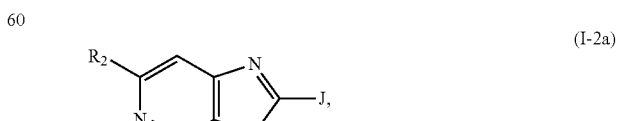

(I-2a)

wherein J is as defined under Embodiment (B2) above;

$R_1$ is $C_1$-$C_4$alkyl;
$R_2$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy or $C_1$-$C_4$haloalkyl;
X is as defined under formula I above;
$G_3$ is N—$R_6$, wherein $R_6$ is as defined under formula I above;
$A_2, A_3, A_4$ and $A_5$, independently from each other, represents $CR_3$ or N; and
$R_3$ is hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (B5)

Further preferred are compounds of formula I-2a

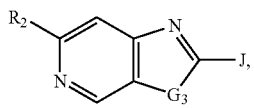
(I-2a)

wherein J is as defined under Embodiment (B2) above;
$R_1$ is $C_1$-$C_4$ alkyl;
$R_2$ is —$OCF_3$, —$SCF_3$, —$S(O)CF_3$, —$S(O)_2CF_3$ or $CF_3$;
X is as defined under formula I above; and
$G_3$ is N—$R_6$, wherein $R_6$ is as defined under formula I above;
$A_2, A_3, A_4$ and $A_5$, independently from each other, represents $CR_3$ or N; and
$R_3$ is hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (B6)

Further preferred are compounds of formula I-2a

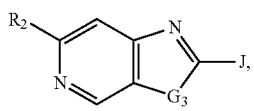
(I-2a)

wherein J is as defined under Embodiment (B2) above;
$R_1$ is ethyl;
$R_2$ is $CF_3$;
X is as defined under formula I above;
$G_3$ is N—$R_6$, wherein $R_6$ is as defined under formula I above;
$A_2, A_3, A_4$ and $A_5$, independently from each other, represents $CR_3$ or N; and
$R_3$ is hydrogen, bromo, chloro, iodo, fluoro, cyano, methyl, ethyl, isopropyl, propyl, trifluoromethyl, $CF_3CH_2$—, $CH_3O$, —$SCF_3$, —$S(O)CF_3$ or —$S(O)_2CF_3$.

EMBODIMENT (B7)

Further preferred are compounds of formula I-2a

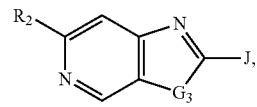
(I-2a)

wherein J is as defined under Embodiment (B2) above;
$R_1$ is ethyl;
$R_2$ is $CF_3$;
X is as defined under formula I above;
$G_3$ is N—$R_6$, wherein $R_6$ is as defined under formula I above;
$A_2, A_3, A_4$ and $A_5$, independently from each other, represents $CR_3$ or N; and
$R_3$ is hydrogen, bromo, chloro, iodo, fluoro, cyano, methyl, or trifluoromethyl.

EMBODIMENT (B8)

Further preferred are compounds of formula I-2a

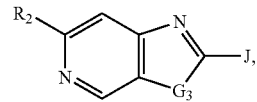
(I-2a)

wherein J is as defined under Embodiment (B2) above;
$R_1$ is ethyl;
$R_2$ is $CF_3$;
X is as defined under formula I above;
$G_3$ is N—$R_6$, $R_6$ is as defined under formula I above;
$A_2, A_3, A_4$ and $A_5$, independently from each other, represents $CR_3$ or N; and
$R_3$ is hydrogen in all groups J.

In all of the preferred embodiments of formula I-2 above, X is preferably S or $SO_2$ and $R_6$ is preferably methyl.

A preferred group of compounds of formula I is represented by the compounds of formula I-3

(I-3)

wherein the substituents X, A, $R_1$, $R_2$, $G_3$, $A_1$, $A_2$, $A_3$, $A_4$ and $A_5$ are as defined under formula I above.

EMBODIMENT (C1)

Preferred are compounds of formula I-3, wherein
$A_1$ represents S, O or $NCH_3$;
$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl; and X, $G_3$, $A_2$, $A_3$, $A_4$ and $A_5$ are as defined under formula I above.

EMBODIMENT (C2)

Further preferred are compounds of formula I-3a

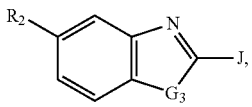
(I-3a)

wherein J is selected from the group consisting of

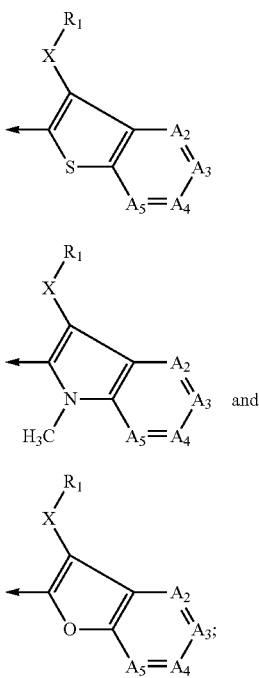

J1

J2 and

J3 wherein $G_3$, $R_1$, $R_2$, X, $A_2$, $A_3$, $A_4$ and $A_5$ are as defined under Embodiment (C1) above.

EMBODIMENT (C3)

Further preferred are compounds of formula I-3a

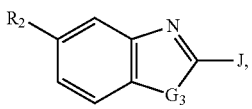
(I-3a)

wherein J is as defined under Embodiment (C2) above;
$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or $C_3$-$C_6$cycloalkyl;

X and $G_3$ is as defined under formula I above;
$A_2$, $A_3$, $A_4$ and $A_5$, independently from each other, represents $CR_3$ or N; and $R_3$ is hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (C4)

Further preferred are compounds of formula I-3a

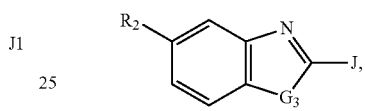
(I-3a)

wherein J is as defined under Embodiment (C2) above;
$R_1$ is $C_1$-$C_4$alkyl;
$R_2$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy or $C_1$-$C_4$haloalkyl;
X is as defined under formula I above;
$G_3$ is N—$R_6$, wherein $R_6$ is as defined under formula I above;
$A_2$, $A_3$, $A_4$ and $A_5$, independently from each other, represents $CR_3$ or N; and $R_3$ is hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (C5)

Further preferred are compounds of formula I-3a

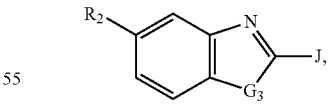
(I-3a)

wherein J is as defined under Embodiment (C2) above;
$R_1$ is $C_1$-$C_4$ alkyl;
$R_2$ is —$OCF_3$, —$SCF_3$, —$S(O)CF_3$, —$S(O)_2CF_3$ or $CF_3$;
X is as defined under formula I above;
$G_3$ is N—$R_6$, wherein $R_6$ is as defined under formula I above;
$A_2$, $A_3$, $A_4$ and $A_5$, independently from each other, represents $CR_3$ or N; and $R_3$ is hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (C6)

Further preferred are compounds of formula I-3a

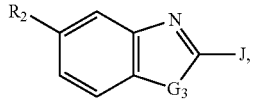
(I-3a)

wherein J is as defined under Embodiment (C2) above;
$R_1$ is ethyl;
$R_2$ is $CF_3$;
X is as defined under formula I above;
$G_3$ is N—$R_6$, wherein $R_6$ is as defined under formula I above;
$A_2, A_3, A_4$ and $A_5$, independently from each other, represents $CR_3$ or N; and
$R_3$ is hydrogen, bromo, chloro, iodo, fluoro, cyano, methyl, ethyl, isopropyl, propyl, trifluoromethyl, $CF_3CH_2$—, $CH_3O$, —$SCF_3$, —$S(O)CF_3$ or —$S(O)_2CF_3$.

EMBODIMENT (C7)

Further preferred are compounds of formula I-3a

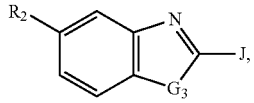
(I-3a)

wherein J is as defined under Embodiment (C2) above;
$R_1$ is ethyl;
$R_2$ is $CF_3$;
X is as defined under formula I above;
$G_3$ is N—$R_6$, wherein $R_6$ is as defined under formula I above;
$A_2, A_3, A_4$ and $A_5$, independently from each other, represents $CR_3$ or N; and
$R_3$ is hydrogen, bromo, chloro, iodo, fluoro, cyano, methyl, or trifluoromethyl.

EMBODIMENT (C8)

Further preferred are compounds of formula I-3a

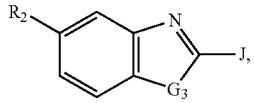
(I-3a)

wherein J is as defined under Embodiment (C2) above;
$R_1$ is ethyl;
$R_2$ is $CF_3$;
X is as defined under formula I above;
$G_3$ is N—$R_6$, $R_6$ is as defined under formula I above;
$A_2, A_3, A_4$ and $A_5$, independently from each other, represents $CR_3$ or N; and
$R_3$ is hydrogen in all groups J.

In all of the preferred embodiments of formula I-1 above, X is preferably S or $SO_2$ and $R_6$ is preferably methyl.

A preferred group of compounds of formula I is represented by the compounds of formula I-4

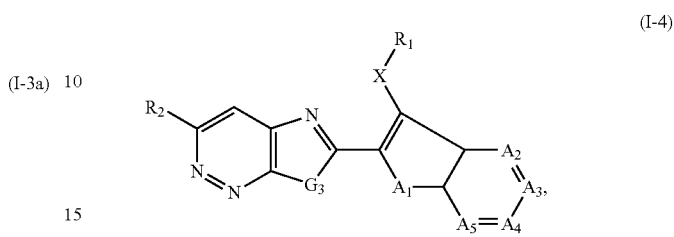
(I-4)

wherein the substituents X, A, $R_1$, $R_2$, $G_3$, $A_1$ $A_2$, $A_3$, $A_4$ and $A_5$ are as defined under formula I above.

EMBODIMENT (D1)

Preferred are compounds of formula I-3, wherein
$A_1$ represents S, O or $NCH_3$;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl; and
X, $G_3$, $A_2$, $A_3$, $A_4$ and $A_5$ are as defined under formula I above.

EMBODIMENT (D2)

Further preferred are compounds of formula I-4a

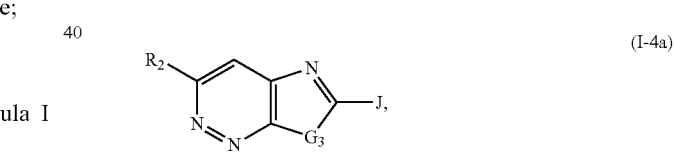
(I-4a)

wherein J is selected from the group consisting of

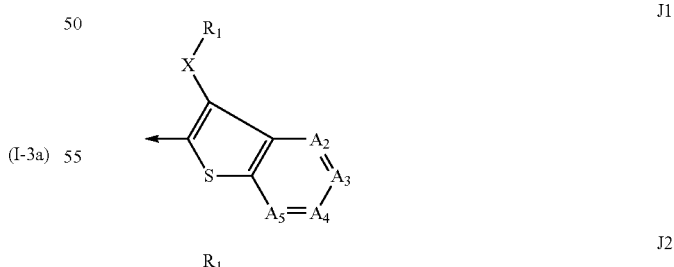
J1

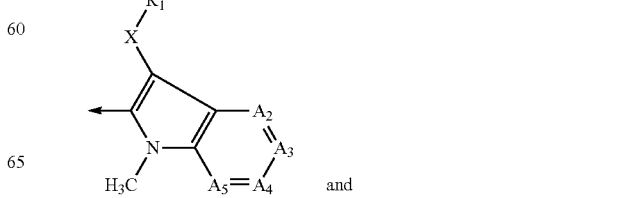
J2 and

-continued

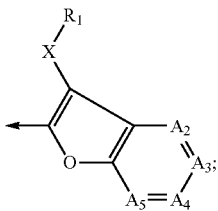

wherein $G_3$, $R_1$, $R_2$, X, $A_2$, $A_3$, $A_4$ and $A_5$ are as defined under Embodiment (D1) above.

EMBODIMENT (D3)

Further preferred are compounds of formula I-4a

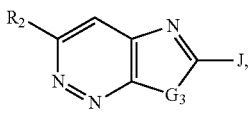
(I-4a)

wherein J is as defined under Embodiment (D2) above;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or $C_3$-$C_6$cycloalkyl;
X and $G_3$ is as defined under formula I above;
$A_2$, $A_3$, $A_4$ and $A_5$, independently from each other, represents $CR_3$ or N; and
$R_3$ is hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (D4)

Further preferred are compounds of formula I-4a

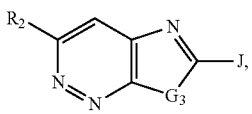
(I-4a)

wherein J is as defined under Embodiment (D2) above;
$R_1$ is $C_1$-$C_4$alkyl;
$R_2$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy or $C_1$-$C_4$haloalkyl;
X is as defined under formula I above;
$G_3$ is N—$R_6$, wherein $R_6$ is as defined under formula I above;
$A_2$, $A_3$, $A_4$ and $A_5$, independently from each other, represents $CR_3$ or N; and
$R_3$ is hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (D5)

Further preferred are compounds of formula I-4a

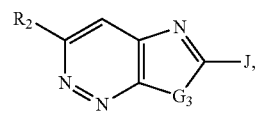
(I-4a)

wherein J is as defined under Embodiment (D2) above;
$R_1$ is $C_1$-$C_4$alkyl;
$R_2$ is —$OCF_3$, —$SCF_3$, —$S(O)CF_3$, —$S(O)_2CF_3$ or $CF_3$;
X is as defined under formula I above;
$G_3$ is N—$R_6$, wherein $R_6$ is as defined under formula I above;
$A_2$, $A_3$, $A_4$ and $A_5$, independently from each other, represents $CR_3$ or N; and
$R_3$ is hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (D6)

Further preferred are compounds of formula I-4a

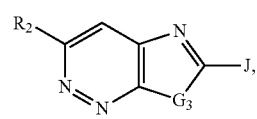
(I-4a)

wherein J is as defined under Embodiment (D2) above;
$R_1$ is ethyl;
$R_2$ is $CF_3$;
X is as defined under formula I above;
$G_3$ is N—$R_6$, wherein $R_6$ is as defined under formula I above;
$A_2$, $A_3$, $A_4$ and $A_5$, independently from each other, represents $CR_3$ or N; and
$R_3$ is hydrogen, bromo, chloro, iodo, fluoro, cyano, methyl, ethyl, isopropyl, propyl, trifluoromethyl, $CF_3CH_2$—, $CH_3O$, —$SCF_3$, —$S(O)CF_3$ or —$S(O)_2CF_3$.

EMBODIMENT (D7)

Further preferred are compounds of formula I-4a

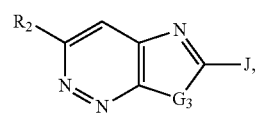
(I-4a)

wherein J is as defined under Embodiment (D2) above;

$R_1$ is ethyl;

$R_2$ is $CF_3$;

X is as defined under formula I above;

$G_3$ is $N-R_6$, wherein $R_6$ is as defined under formula I above;

$A_2, A_3, A_4$ and $A_5$, independently from each other, represents $CR_3$ or N; and $R_3$ is hydrogen, bromo, chloro, iodo, fluoro, cyano, methyl, or trifluoromethyl.

EMBODIMENT (D8)

Further preferred are compounds of formula I-4a

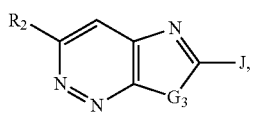
(I-4a)

wherein J is as defined under Embodiment (D2) above;

$R_1$ is ethyl;

$R_2$ is $CF_3$;

X is as defined under formula I above;

$G_3$ is $N-R_6$, $R_6$ is as defined under formula I above;

$A_2, A_3, A_4$ and $A_5$, independently from each other, represents $CR_3$ or N; and $R_3$ is hydrogen in all groups J.

In all of the preferred embodiments of formula I-1 above, X is preferably S or $SO_2$ and $R_6$ is preferably methyl.

In all of the preferred embodiments A2-A8, B2-B8, C2-C8 and D2-D8, J is preferably J1, J2, J3, in particular J is J1.

More preferred compounds of formula I are represented by the compounds selected from the formulae I-1a, I-2a and I-3a

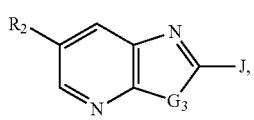
(I-1a)

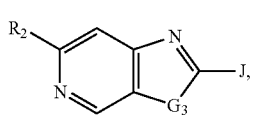
(I-2a)

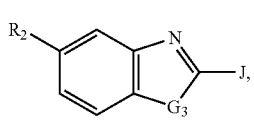
(I-3a)

wherein J is as defined as

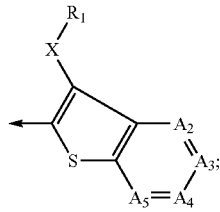
J1

$R_2$ is $C_1$-$C_2$haloakyl, $C_1$-$C_2$haloalkylsulfanyl, $C_1$-$C_2$haloalkylsulfinyl or $C_1$-$C_2$haloalkylsulfonyl; preferably $C_1$-$C_2$haloakyl or $C_1$-$C_2$haloalkylsulfanyl;

$G_3$ is $N-R_6$, wherein $R_6$ is $C_1$-$C_2$alkyl;

$A_2, A_3, A_4$ and $A_5$, independently from each other, are $CR_3$ or N, preferably $CR_3$, wherein $R_3$ is $C_1$-$C_4$ haloalkyl, hydrogen, halogen, cyclopropyl or pyrazolyl, or cyclopropyl or pyrazolyl which can be substituted by $C_1$-$C_2$ haloakyl.

The process according to the invention for preparing compounds of formula (I) is carried out by methods known to those skilled in the art, or described for example in WO 2009/131237, WO 2011/043404, WO 2011/040629, WO 2010/125985, WO 2012/086848, WO 2013/018928, WO 2013/191113, WO 2013/180193 and WO 2013/180194, and comprises the reaction of a compound of formula II,

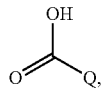
(II)

wherein Q is the group

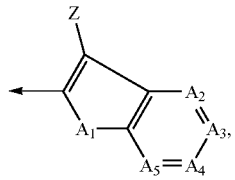
(Q)

wherein Z is $X-R_1$ or a leaving group, for example a halogen, and wherein X, $R_1$, $A_1$, $A_2$, $A_3$, $A_4$ and $A_5$ are as described under formula I above, and wherein the arrow in the radical Q shows the point of attachment to the carbon atom of the carboxyl group in the compound of formula II, with a compound of formula III,

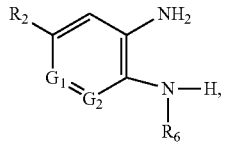
(III)

wherein $R_6$, $R_2$, $G_1$ and $G_2$ are as described under formula I above, in the presence of a dehydrating agent, such as for example polyphosphoric acid at temperature between 150° C. to 250° C., to yield compounds of formula Ia, wherein the substituents are as described above and under formula I.

Such processes are well known and have been described for example in WO 2008/128968 or WO 2006/003440. The process is summarized in scheme 1 for compounds of formula Ia:

Scheme 1

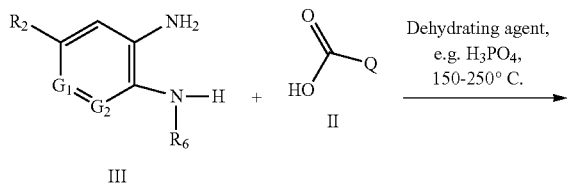

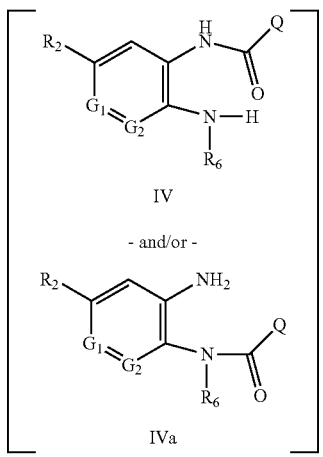

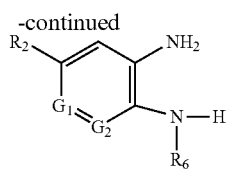

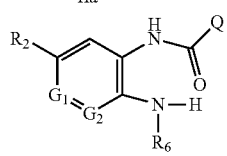

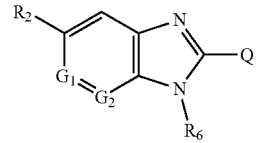

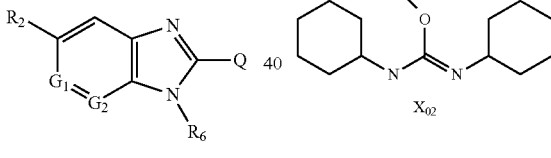

As can be seen in scheme 1, the formation of compounds of formula Ia occurs through the intermediacy of a compound of formula IV (and/or its position isomer IVa). Intermediate IV or intermediate IVa may form as a pure entity, or intermediates IV and IVa may arise as a mixture of regioisomeric acylation products. It is in many cases advantageous to thus prepare compounds of formula (I) through such intermediates IV/IVa, which may be isolated and optionally purified. This is illustrated for compounds of formula Ia in scheme 2:

Scheme 2

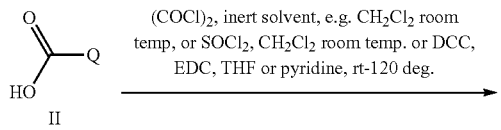

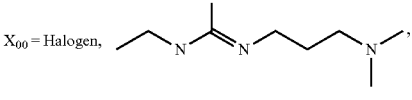

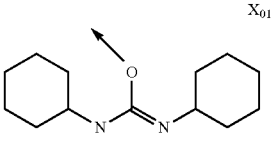

Compounds of the formula IV and/or IVa (or a mixture thereof), or a salt thereof, wherein Q is as defined above, and wherein $R_6$, $R_2$, $G_1$ and $G_2$ are as described under formula I above, may be prepared by i) activation of compound of formula II, wherein Q is as defined above, by methods known to those skilled in the art and described in, for example, Tetrahedron, 2005, 61 (46), 10827-10852, to form an activated species IIa, wherein Q is as defined above and wherein $X_{00}$ is halogen, preferably chlorine. For example, compounds IIa where $X_{00}$ is halogen, preferably chlorine, are formed by treatment of II with, for example, oxalyl chloride (COCl)$_2$ or thionyl chloride SOCl$_2$ in the presence of catalytic quantities of N,N-dimethylformamide DMF in inert solvents such as methylene chloride CH$_2$Cl$_2$ or tetrahydrofuran THF at temperatures between 20 to 100° C., preferably 25° C. Alternatively, treatment of compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_6$, $R_2$, $G_1$ and $G_2$ are as described under formula I above, optionally in the presence of a base, such as triethylamine or pyridine, in an inert solvents such as dichloromethane, tetrahydrofuran, dioxane or toluene, at temperatures between 0 and 80° C., to form the compounds of formula IV and/or IVa (or a mixture thereof).

Compounds of formula IV and/or IVa (or a mixture thereof) may further be converted into compounds of formula Ia, wherein Q is as defined above, and wherein $R_6$, $R_2$, $G_1$ and $G_2$ are as described under formula I above, by dehydration, eg. by heating the compounds IV and/or IVa (or a mixture thereof) in the presence of an acid catalyst, such as for example methane sulfonic acid, or para-toluene sulfonic acid TsOH, in an inert solvent such as N-methyl pyrrolidine NMP at temperatures between 25-180° C., preferably 100-170° C., optionally under microwave conditions. Such processes have been described previously, for example, in WO 2010/125985.

Compounds of formula Ia, wherein Z is a leaving group, for example halogen, preferably fluorine or chlorine, and wherein $R_6$, $R_2$, $G_1$ and $G_2$ are as described under formula I above, can be reacted with compounds of formula V

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, wherein $R_1$ is as described under formula I above, and in which $R_6$, $A_1$, $R_2$, $A_2$, $A_3$, $A_4$, $A_5$, $G_1$ and $G_2$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO2013/018928. Examples of salts of the compound of formula V include compounds of the formula Va

wherein $R_1$ is as defined above and wherein M is, for example, sodium or potassium. This is illustrated for compounds of formula Ib in scheme 3:

Scheme 3

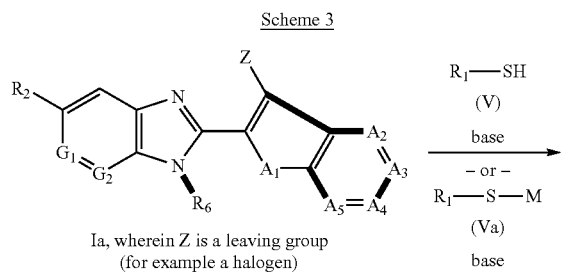

Ia, wherein Z is a leaving group
(for example a halogen)

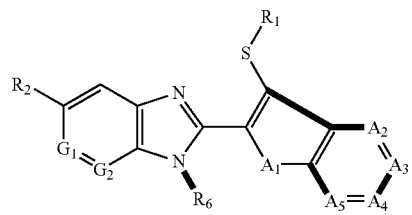

Ib, that is a compound of formula I
wherein X is sulfur (a sulfide)

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of of the sulfide compounds Ib to produce the sulfone compounds I (wherein X=$SO_2$). Such oxidation reactions are disclosed, for example, in WO 2013/018928.

Compounds of formula VIa, wherein Z is X—$R_1$ or a leaving group, for example halogen, and wherein X, $R_1$, $R_2$, $R_6$, $G_1$, $G_2$, $A_1$, $A_2$, $A_3$, $A_4$ and $A_5$ are as described under formula I above, may be prepared by reaction between compounds of formula II respectively IIa, wherein Z is X—$R_1$ or a leaving group, for example halogen, and wherein X, $R_1$ and A are as described under formula I above, and in which $X_{00}$ is as described above, and compounds of formula IIIa, wherein $R_6$ and $R_2$ are as described under formula I above, under similar conditions as for the preparation of compounds of formula Ia from compounds of formula II/IIa and III described above (see scheme 1 and 2). This is illustrated for compounds of formula VIa in scheme 4:

Scheme 4

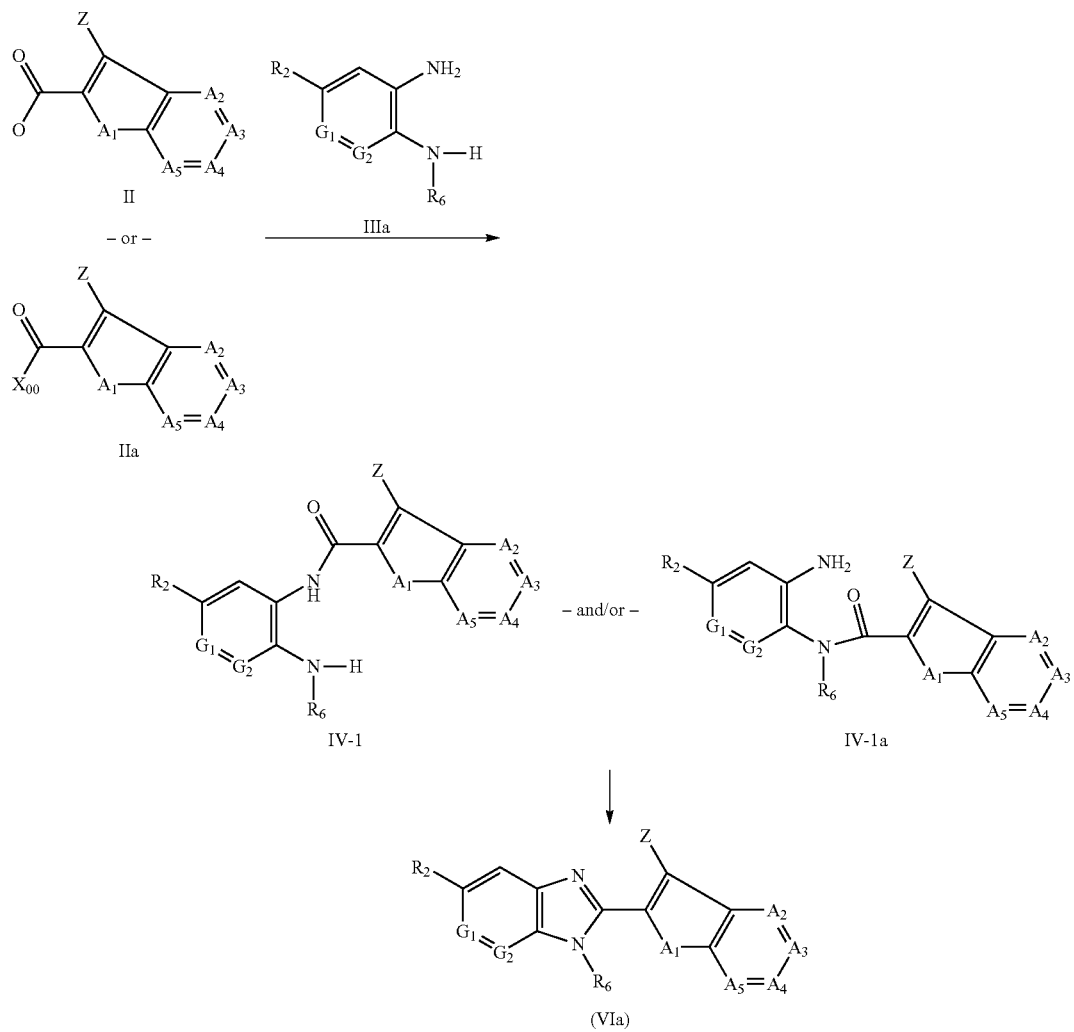

Analogously to descriptions in schemes 1 and 2, the formation of compounds of formula VIa occurs through the intermediacy of compounds of formula IV-1 and/or IV-Ia (or a mixture thereof), or salts thereof, which optionally may be isolated and purified.

Diamino compounds of formula III are

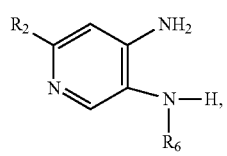

IIIa

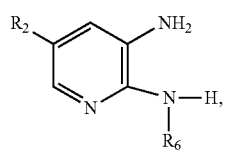

IIIb

-continued

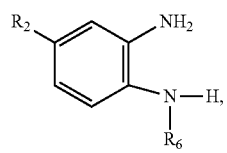

IIIc

Diamino compounds of formula IIIb and IIIc are either known, commercially available or may be made by methods known to a person skilled in the art. See for example, IIIB wherein $R_6$ is methyl, is commercially available (CAS 172648-55-4) and it synthesis is described, for example, in US2012178779 (WO 2010125985). Another example is IIIC wherein $R_6$ is methyl, is commercially available (CAS 35203-49-7).

Compounds of the formula IIIa, wherein $R_6$, and $R_2$ are as described under formula I above, may be prepared from diamino compounds of formula VII, wherein $R_2$ is as described under formula I above, by means of a direct alkylation with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile (scheme 5).

Scheme 5

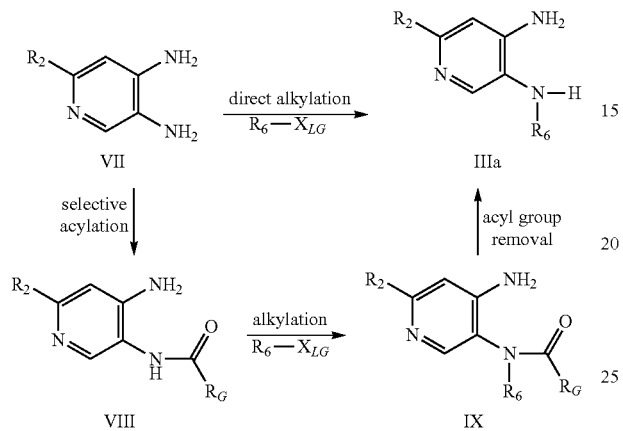

Alternatively, the sequence to prepare compounds of formula IIIa from compounds of formula VII, may involve i. a selective acylation of compound VII to form a compound of formula VIII, wherein $R_2$ is as described under formula I above and wherein the acylation agent is for example di-tert-butyl dicarbonate (leading to compound VIII wherein $R_G$ is tert-butyloxy), in an ether solvent, such as for example, tetrahydrofuran or dioxane; ii. alkylation of compound VIII with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IX, wherein $R_6$ and $R_2$ are as described under formula I above and wherein $R_G$ is for example tert-butyloxy; and finally iii. deacylation of compound IX to form the compound of formula IIIa, wherein $R_6$, and $R_2$ are as described under formula I above. When $R_G$ is for example tert-butyloxy, conditions for the acyl group removal include, for example, treatment of compound IX with hydrogen halide, in particular hydrogen chloride or hydrogen bromide, in solvents such as ethers (for example diethyl ether, tetrahydrofuran or dioxane) or acetic acid. Alternatively, compound IX may also be treated with, for example, trifluoroacetic acid, in optional presence of an inert solvent, such as for example dichloromethane or chloroform, to form a compound of formula IIIa.

This alternative approach to prepare compounds of formula IIIa is described in more details in scheme 6 for the particular situation where $R_2$ is $CF_3$, $R_6$ is $CH_3$, and $R_G$ is tert-butyloxy:

Scheme 6

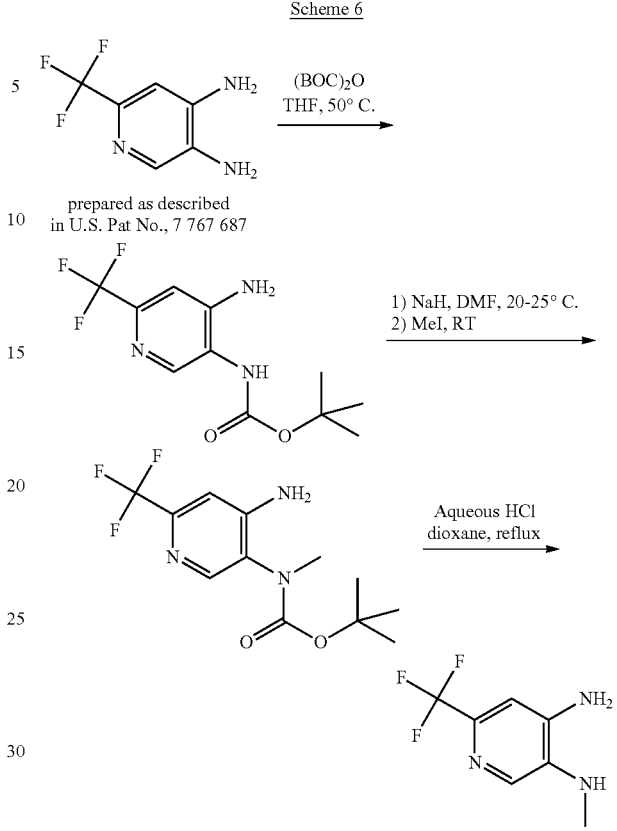

Common abbreviations
$(BOC)_2O$ = di-tert-butyl dicarbonate; THF = tetrahydrofuran; NaH = sodium hydride; DMF = N,N-dimethylformamide; MeI = methyl iodide; RT = room temperature; HCl = hydrogen chloride.

Diamino compounds of formula (VII) are either known, commercially available or may be made by methods known to a person skilled in the art, for example in analogy to a preparation method described in U.S. Pat. No. 7,767,687.

Compounds of formula II,

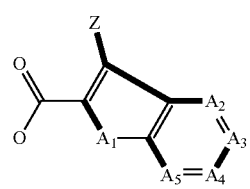

II wherein Z is X—$R_1$ or a leaving group or a group that could be transformed in leaving group such as, for example halogen, amine or nitro, and wherein X, $R_1$, $A_1$, $A_2$, $A_3$, $A_4$ and $A_5$ are as described under formula I above, may be either known, commercially available or may be made by methods known to a person skilled in the art.

Compounds of formula IIc, wherein Z is a leaving group, for example halogen, preferably fluorine, chlorine, and wherein $A_1$, $A_2$, $A_3$, $A_4$ and $A_5$ are as described under formula I above, and wherein R is alkyl or hydrogen can be transformed in compounds of formula IId by reaction with compounds of formula V $R_1$—SH  (V), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula IId, wherein R is alkyl or hydrogen, $R_1$ is as described under formula I above, and in which $A_1$, $A_2$, $A_3$, $A_4$ and $A_5$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula V include compounds of the formula Va $R_1$—S-M     (Va), wherein $R_1$ is as defined above and wherein M is, for example, sodium or potassium. This is illustrated for compounds of formula IId in scheme 7:

Scheme 7

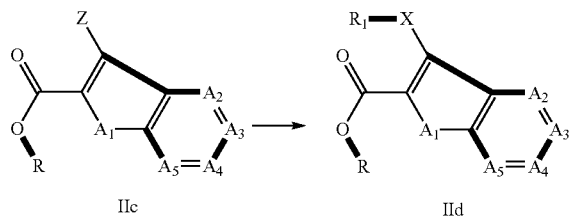

IIc         IId

Alternatively, compounds of formula IIc, wherein Z is a amine and wherein $A_1$, $A_2$, $A_3$, $A_4$ and $A_5$ are as described under formula I above, and wherein R is alkyl or hydrogen can be transformed to compounds of formula IId via diazotation and reaction with dialkyldisulfide. This transformation is well known and could be made by methods known to a person skilled in the art (see for example: Synthetic Communications, 31(12), 1857-1861; 2001 or Organic & Biomolecular Chemistry, 6(4), 745-761; 2008).

Compounds of formula IIc, wherein Z is a amine and wherein $A_1$, $A_2$, $A_3$, $A_4$ and $A_5$ are as described under formula I above, and wherein R is alkyl or hydrogen can be transformed to compounds of formula IIe via diazotation and reaction with sodium sulphide, followed by reduction. This transformation is well known and could be made by methods known to a person skilled in the art (see for example: US 20040116734 or Chemische Berichte, 120(7), 1151-73; 1987). Alkylation of compound IIe with $R_1$—$X_{LG}$, wherein $R_1$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IId, wherein $R_1$ is as described under formula I above. See scheme 8.

Scheme 8

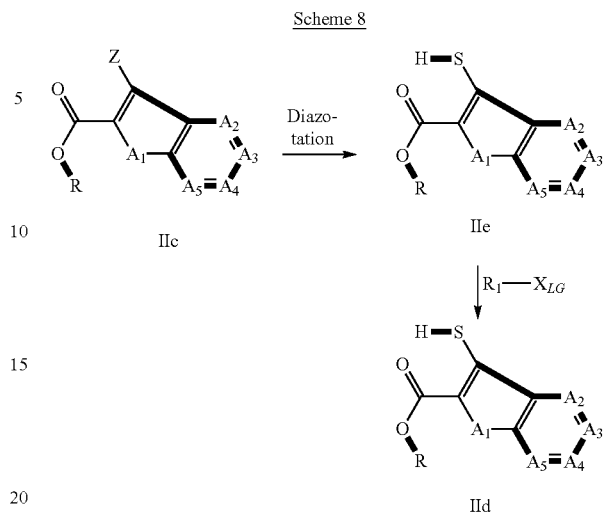

Compound of formula (II) may be prepared by reaction of a compound of formula (IId), wherein R is alkyl via hydrolysis. For instance, in the case where R is methyl or ethyl, the hydrolysis can be done with water and a base, such as potassium hydroxide or lithium hydroxide, in the absence or in the presence of a solvent, such as, for instance, tetrahydrofuran or methanol. In the case where R is, for example, tert-butyl, the hydrolysis is done in the presence of acid, such as trifluoroacetic acid or hydrochloric acid. The reaction is carried out at a temperature of from −120° C. to +130° C., preferably from −100° C. to 100° C. See scheme 9.

Scheme 9

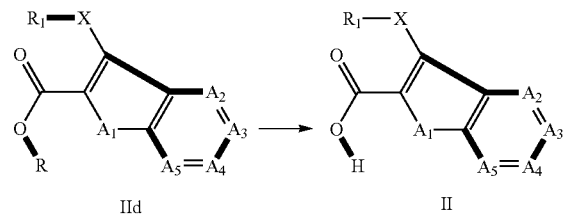

IId         II

Alternatively, compound of formula II may be prepared by reaction of a compound of formula (X) wherein Z is a leaving group as nitro or halogen such as fluorine and wherein $A_1$, $A_2$, $A_3$, $A_4$ and $A_5$ are as described under formula I above by reaction of a compound of formula V or Va $R_1$—SH     (V), to give compounds of formula Xd or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula XIIb, wherein $R_1$ is as described under formula I above, and in which $A_1$, $A_2$, $A_3$, $A_4$ and $A_5$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula V include compounds of the formula Va $R_1$—S-M  (Va), wherein $R_1$ is as defined above and wherein M is, for example, sodium or potassium. Compounds of formula II may be prepared by hydrolysis of the cyano of compound of formula Xd in acidic or basic conditions. This transformation is well known and could be made by methods known to a person skilled in the art (see for example: Comprehensive Organic Transformations: A Guide to Functional Group Preparations. Edited by Richard C. Larock 1989 p 993, VCH publishers). This is illustrated for compounds of formula II in scheme 10.

Scheme 10

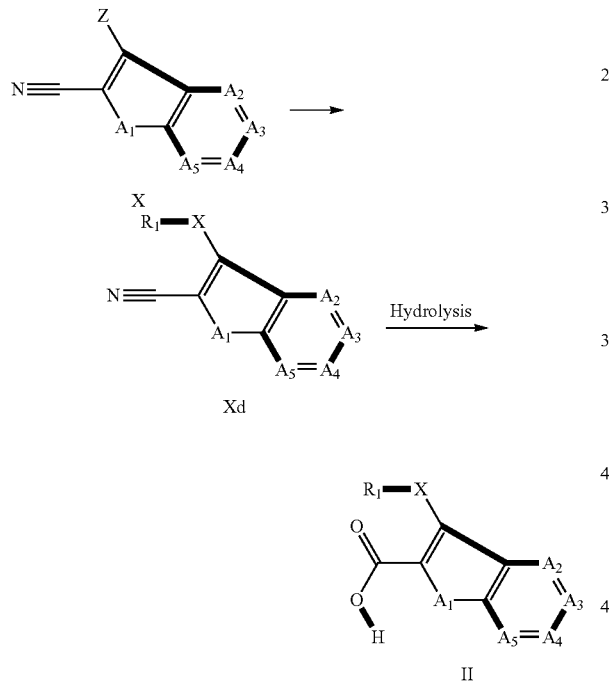

Compounds of formula X are either known, commercially available or may be made by methods known to a person skilled in the art.

Alternatively, compound of formula II may be prepared by reaction of a compound of formula (XI) where in Z is a leaving group as nitro or halogen such as fluorine and wherein $A_1$, $A_2$, $A_3$, $A_4$ and $A_5$ are as described under formula I above by oxidation in presence of a oxidant such as oxygen, hydrogen peroxide or an metal oxide such as chromium trioxide with or without acid such as sulphuric acid with or without metal catalyst. This transformation is well known and could be made by methods known to a person skilled in the art (see for example: Comprehensive Organic Transformations: A Guide to Functional Group Preparations. Edited by Richard C. Larock 1989 p 823, VCH publishers). This is illustrated for compounds of formula II in scheme 11.

Scheme 11

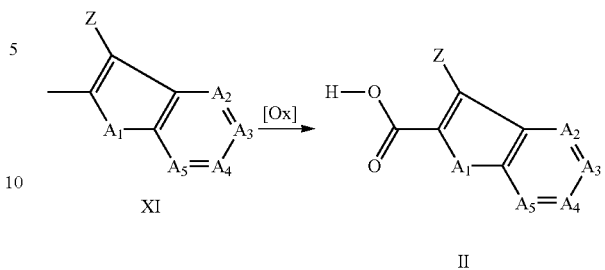

Compounds of formula XI are either known, commercially available or may be made by methods known to a person skilled in the art.

Compounds of formula I may be prepared by reaction of a compound of formula (I) wherein $A_1$, $R_1$, $G_1$, $G_2$, $G_3$ and X are as described under formula I above and wherein, at least, one of the $A_2$, $A_3$, $A_4$ or $A_5$ is C—Z, wherein Z is a leaving group such as bromide or chlorine by classical reactions, known to a person skilled in the art, such as for example Suzuki, Stille or Ulmann coupling, introduction of haloalkylsulfure group or polyhalogenate chain, This is exemplified, but not limited, in the following schemes and comments when $A_4$ is a carbon linked to an leaving group Xb1.

Compounds of formula Iaa wherein $A_4$ is a carbon linked to a pyrazolyl and wherein are as defined in formula I, can be prepared from compounds of formula Ic, wherein $A_1$, $A_2$, $A_3$ and $A_5$ are as described under formula I above and $R_1$, $R_2$, $G_1$, $G_2$, X, and $R_6$ are as defined in formula I, and $Xb_1$ is a leaving group such as chlorine, bromine or iodine, or an aryl- or alkylsulfonate such as trifluoromethanesulfonate by reacting an pyrazolyl optionally substituted, in the presence of a base, for example an alkaline metal hydride such as sodium hydride, or an alkali metal carbonate, for example cesium or potassium carbonate, in the presence or not of a copper catalyst, for example copper (I) iodide in an inert solvent such as N-methyl pyrollidone or DMF at temperatures between 30-150° C. The reaction is illustrated in scheme 12

Scheme 12

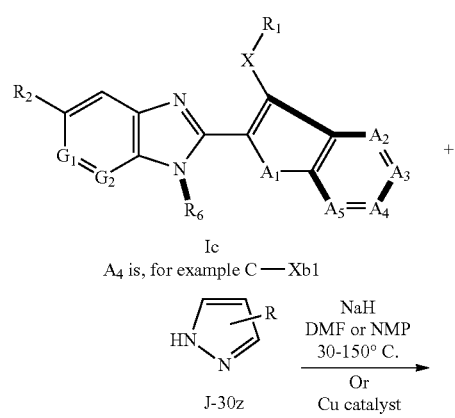

-continued

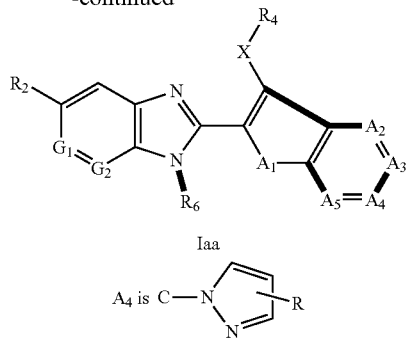

Iaa

A₄ is C—N(pyrazole)—R

Another examples to preparing compounds of formula I is carried out in principle by methods known to those skilled in the art, and as described below:

Compounds of formula I, wherein $A_1$, $A_2$, $A_3$ and $A_5$, $R_1$, $R_2$, $G_1$, $G_2$, X, and $R_6$ are as defined in formula I, and $A_4$ is for example, Cyclopropyl, can prepared (as shown in scheme 13) by a Suzuki reaction, which involves for example, reacting compounds of formula Ic, wherein $Xb_1$ is a leaving group, for example, chlorine, bromine or iodine, or an aryl- or alkylsulfonate such as trifluoromethanesulfonate with compounds of formula XIIa, wherein $Y_{b1}$ can be a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water, or of dioxane and water, preferably under an inert atmosphere. The reaction temperature can preferentially range from room temperature to the boiling point of the reaction mixture. Such Suzuki reactions are well known to those skilled in the art and have been reviewed, for example *J. Orgmet. Chem.* 576, 1999, 147-168.

-continued

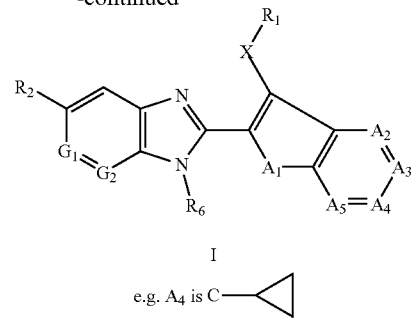

I e.g. A₄ is C—(cyclopropyl)

Alternatively compounds of formula I can be prepared by a Stille reaction of compounds of formula XIIb wherein $Y_{b2}$ is a trialkyl tin derivative, preferably tri-n-butyl tin, with compounds of formula II. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, J. Org. Chem., 2009, 74, 5599-5602, and *Angew. Chem. Int. Ed.*, 2004, 43, 1132-1136.

Another example is that compounds of formula I, wherein $A_1$, $A_2$, $A_3$ and $A_5$, $R_1$, $R_2$, $G_2$, X, and $R_6$ are as defined in formula I, and $A_4$ is for example, $C_1$-$C_4$haloalkylsulfanyl or $C_2$-$C_4$haloalkyl, can prepared (as shown in scheme 13) by reaction with compounds of formula Ic, wherein $Xb_1$ is a leaving group, for example, chlorine, bromine or iodine, or an aryl- or alkylsulfonate such as trifluoromethanesulfonate with copper complex catalyst such as, for example, (bpy)CuSR₇ or the Pentafluoroethylator, wherein $R_7$ is $C_1$-$C_3$ haloalkyl. Such chemistry is known and has been described in the literature (*Angew. Chem. Int. Ed.* 2013, 52, 1548-1552), Angewandte Chemie, International Edition, 51(2), 536-539, S536/1-S536/54; 2012 or Organic Letters, 16(6), 1744-1747; 2014.

Scheme 13:

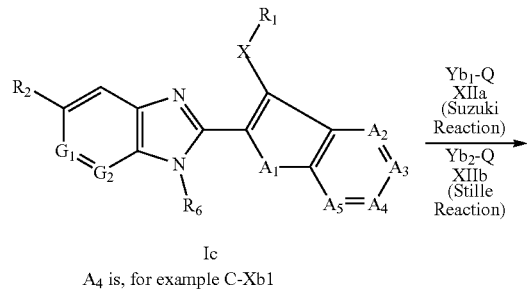

Ic
A₄ is, for example C-Xb1

$Yb_1$-Q XIIa (Suzuki Reaction)
$Yb_2$-Q XIIb (Stille Reaction)

Scheme 14.

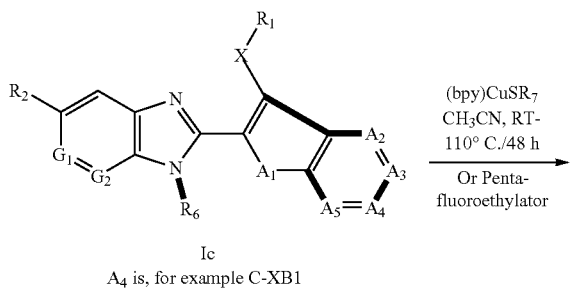

Ic
A₄ is, for example C-XB1

(bpy)CuSR₇
CH₃CN, RT-110° C./48 h

Or Pentafluoroethylator

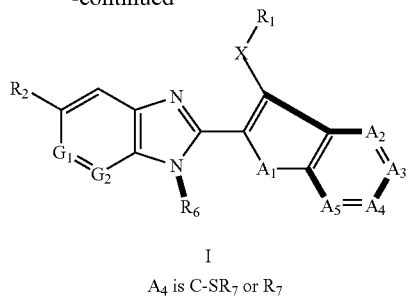

I

A$_4$ is C-SR$_7$ or R$_7$

For preparing all other compounds of the formula (I) functionalized according to the definitions of formula III, II and Q, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 4 below can be prepared according to the methods described above. The examples which follow are intended to illustrate the invention and show preferred compounds of formula I. "Ph" represents the phenyl group.

Table 1:

This table discloses the 27 compounds of the formula I-1a:

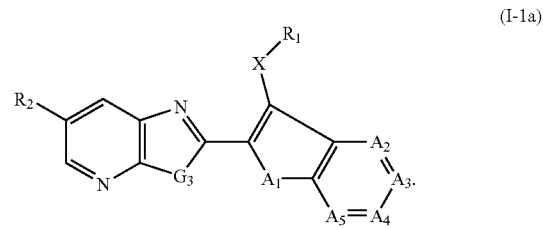
(I-1a)

TABLE 1

| Comp. No. | X | $R_1$ | $A_1$ | $R_2$ | $A_2$ | $A_3$ | $A_4$ | $A_5$ | $G_3$ |
|---|---|---|---|---|---|---|---|---|---|
| 1.001 | S | —$CH_2CH_3$ | S | $CF_3$ | CH | CH | CH | CH | N—$CH_3$ |
| 1.002 | SO | —$CH_2CH_3$ | S | $CF_3$ | CH | CH | CH | CH | N—$CH_3$ |
| 1.003 | $SO_2$ | —$CH_2CH_3$ | S | $CF_3$ | CH | CH | CH | CH | N—$CH_3$ |
| 1.004 | S | —$CH_2CH_3$ | S | —$SCF_3$ | CH | CH | CH | CH | N—$CH_3$ |
| 1.005 | SO | —$CH_2CH_3$ | S | —$SCF_3$ | CH | CH | CH | CH | N—$CH_3$ |
| 1.006 | $SO_2$ | —$CH_2CH_3$ | S | —$SCF_3$ | CH | CH | CH | CH | N—$CH_3$ |
| 1.007 | S | —$CH_2CH_3$ | S | $CF_2CF_3$ | CH | CH | CH | CH | N—$CH_3$ |
| 1.008 | SO | —$CH_2CH_3$ | S | $CF_2CF_3$ | CH | CH | CH | CH | N—$CH_3$ |
| 1.009 | $SO_2$ | —$CH_2CH_3$ | S | $CF_2CF_3$ | CH | CH | CH | CH | N—$CH_3$ |
| 1.010 | S | —$CH_2CH_3$ | S | $CF_3$ | CH | CH | C—$CF_3$ | CH | N—$CH_3$ |
| 1.011 | SO | —$CH_2CH_3$ | S | $CF_3$ | CH | CH | C—$CF_3$ | CH | N—$CH_3$ |
| 1.012 | $SO_2$ | —$CH_2CH_3$ | S | $CF_3$ | CH | CH | C—$CF_3$ | CH | N—$CH_3$ |
| 1.013 | S | —$CH_2CH_3$ | S | —$SCF_3$ | CH | CH | C—$CF_3$ | CH | N—$CH_3$ |
| 1.014 | SO | —$CH_2CH_3$ | S | —$SCF_3$ | CH | CH | C—$CF_3$ | CH | N—$CH_3$ |
| 1.015 | $SO_2$ | —$CH_2CH_3$ | S | —$SCF_3$ | CH | CH | C—$CF_3$ | CH | N—$CH_3$ |
| 1.016 | S | —$CH_2CH_3$ | S | $CF_2CF_3$ | CH | CH | C—$CF_3$ | CH | N—$CH_3$ |
| 1.017 | SO | —$CH_2CH_3$ | S | $CF_2CF_3$ | CH | CH | C—$CF_3$ | CH | N—$CH_3$ |
| 1.018 | $SO_2$ | —$CH_2CH_3$ | S | $CF_2CF_3$ | CH | CH | C—$CF_3$ | CH | N—$CH_3$ |
| 1.019 | S | —$CH_2CH_3$ | S | $CF_3$ | CH | C—$CF_3$ | CH | CH | N—$CH_3$ |
| 1.020 | SO | —$CH_2CH_3$ | S | $CF_3$ | CH | C—$CF_3$ | CH | CH | N—$CH_3$ |
| 1.021 | $SO_2$ | —$CH_2CH_3$ | S | $CF_3$ | CH | C—$CF_3$ | CH | CH | N—$CH_3$ |
| 1.022 | S | —$CH_2CH_3$ | S | —$SCF_3$ | CH | C—$CF_3$ | CH | CH | N—$CH_3$ |
| 1.023 | SO | —$CH_2CH_3$ | S | —$SCF_3$ | CH | C—$CF_3$ | CH | CH | N—$CH_3$ |
| 1.024 | $SO_2$ | —$CH_2CH_3$ | S | —$SCF_3$ | CH | C—$CF_3$ | CH | CH | N—$CH_3$ |
| 1.025 | S | —$CH_2CH_3$ | S | $CF_2CF_3$ | CH | C—$CF_3$ | CH | CH | N—$CH_3$ |
| 1.026 | SO | —$CH_2CH_3$ | S | $CF_2CF_3$ | CH | C—$CF_3$ | CH | CH | N—$CH_3$ |
| 1.027 | $SO_2$ | —$CH_2CH_3$ | S | $CF_2CF_3$ | CH | C—$CF_3$ | CH | CH | N—$CH_3$ | and the N-oxides and tautomers of the compounds of Table 1.

Table 2:

This table discloses the 27 compounds of the formula I-1b:

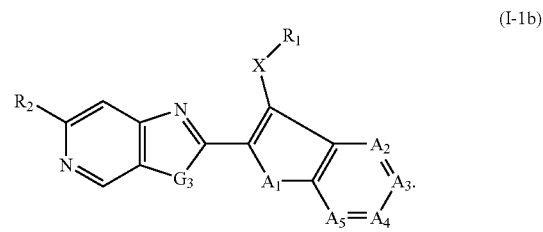
(I-1b)

TABLE 2

| Comp. No. | X | $R_1$ | $A_1$ | $R_2$ | $A_2$ | $A_3$ | $A_4$ | $A_5$ | $G_3$ |
|---|---|---|---|---|---|---|---|---|---|
| 2.001 | S | —CH$_2$CH$_3$ | S | CF$_3$ | CH | CH | CH | CH | N—CH$_3$ |
| 2.002 | SO | —CH$_2$CH$_3$ | S | CF$_3$ | CH | CH | CH | CH | N—CH$_3$ |
| 2.003 | SO$_2$ | —CH$_2$CH$_3$ | S | CF$_3$ | CH | CH | CH | CH | N—CH$_3$ |
| 2.004 | S | —CH$_2$CH$_3$ | S | —SCF$_3$ | CH | CH | CH | CH | N—CH$_3$ |
| 2.005 | SO | —CH$_2$CH$_3$ | S | —SCF$_3$ | CH | CH | CH | CH | N—CH$_3$ |
| 2.006 | SO$_2$ | —CH$_2$CH$_3$ | S | —SCF$_3$ | CH | CH | CH | CH | N—CH$_3$ |
| 2.007 | S | —CH$_2$CH$_3$ | S | CF$_2$CF$_3$ | CH | CH | CH | CH | N—CH$_3$ |
| 2.008 | SO | —CH$_2$CH$_3$ | S | CF$_2$CF$_3$ | CH | CH | CH | CH | N—CH$_3$ |
| 2.009 | SO$_2$ | —CH$_2$CH$_3$ | S | CF$_2$CF$_3$ | CH | CH | CH | CH | N—CH$_3$ |
| 2.010 | S | —CH$_2$CH$_3$ | S | CF$_3$ | CH | CH | C—CF$_3$ | CH | N—CH$_3$ |
| 2.011 | SO | —CH$_2$CH$_3$ | S | CF$_3$ | CH | CH | C—CF$_3$ | CH | N—CH$_3$ |
| 2.012 | SO$_2$ | —CH$_2$CH$_3$ | S | CF$_3$ | CH | CH | C—CF$_3$ | CH | N—CH$_3$ |
| 2.013 | S | —CH$_2$CH$_3$ | S | —SCF$_3$ | CH | CH | C—CF$_3$ | CH | N—CH$_3$ |
| 2.014 | SO | —CH$_2$CH$_3$ | S | —SCF$_3$ | CH | CH | C—CF$_3$ | CH | N—CH$_3$ |
| 2.015 | SO$_2$ | —CH$_2$CH$_3$ | S | —SCF$_3$ | CH | CH | C—CF$_3$ | CH | N—CH$_3$ |
| 2.016 | S | —CH$_2$CH$_3$ | S | CF$_2$CF$_3$ | CH | CH | C—CF$_3$ | CH | N—CH$_3$ |
| 2.017 | SO | —CH$_2$CH$_3$ | S | CF$_2$CF$_3$ | CH | CH | C—CF$_3$ | CH | N—CH$_3$ |
| 2.018 | SO$_2$ | —CH$_2$CH$_3$ | S | CF$_2$CF$_3$ | CH | CH | C—CF$_3$ | CH | N—CH$_3$ |
| 2.019 | S | —CH$_2$CH$_3$ | S | CF$_3$ | CH | C—CF$_3$ | CH | CH | N—CH$_3$ |
| 2.020 | SO | —CH$_2$CH$_3$ | S | CF$_3$ | CH | C—CF$_3$ | CH | CH | N—CH$_3$ |
| 2.021 | SO$_2$ | —CH$_2$CH$_3$ | S | CF$_3$ | CH | C—CF$_3$ | CH | CH | N—CH$_3$ |
| 2.022 | S | —CH$_2$CH$_3$ | S | —SCF$_3$ | CH | C—CF$_3$ | CH | CH | N—CH$_3$ |
| 2.023 | SO | —CH$_2$CH$_3$ | S | —SCF$_3$ | CH | C—CF$_3$ | CH | CH | N—CH$_3$ |
| 2.024 | SO$_2$ | —CH$_2$CH$_3$ | S | —SCF$_3$ | CH | C—CF$_3$ | CH | CH | N—CH$_3$ |
| 2.025 | S | —CH$_2$CH$_3$ | S | CF$_2$CF$_3$ | CH | C—CF$_3$ | CH | CH | N—CH$_3$ |
| 2.026 | SO | —CH$_2$CH$_3$ | S | CF$_2$CF$_3$ | CH | C—CF$_3$ | CH | CH | N—CH$_3$ |
| 2.027 | SO$_2$ | —CH$_2$CH$_3$ | S | CF$_2$CF$_3$ | CH | C—CF$_3$ | CH | CH | N—CH$_3$ | and the N-oxides and tautomers of the compounds of Table 2.

Table 3:

This table discloses the 27 compounds of the formula I-1c:

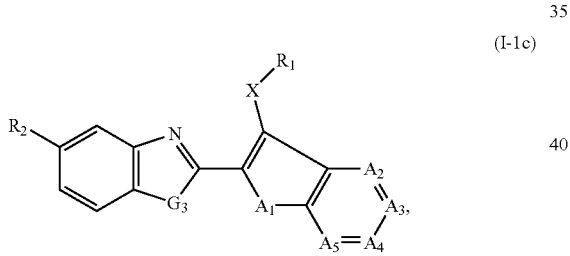

(I-1c)

TABLE 3

| Comp. No. | X | $R_1$ | $A_1$ | $R_2$ | $A_2$ | $A_3$ | $A_4$ | $A_5$ | $G_3$ |
|---|---|---|---|---|---|---|---|---|---|
| 3.001 | S | —CH$_2$CH$_3$ | S | CF$_3$ | CH | CH | CH | CH | N—CH$_3$ |
| 3.002 | SO | —CH$_2$CH$_3$ | S | CF$_3$ | CH | CH | CH | CH | N—CH$_3$ |
| 3.003 | SO$_2$ | —CH$_2$CH$_3$ | S | CF$_3$ | CH | CH | CH | CH | N—CH$_3$ |
| 3.004 | S | —CH$_2$CH$_3$ | S | —SCF$_3$ | CH | CH | CH | CH | N—CH$_3$ |
| 3.005 | SO | —CH$_2$CH$_3$ | S | —SCF$_3$ | CH | CH | CH | CH | N—CH$_3$ |
| 3.006 | SO$_2$ | —CH$_2$CH$_3$ | S | —SCF$_3$ | CH | CH | CH | CH | N—CH$_3$ |
| 3.007 | S | —CH$_2$CH$_3$ | S | CF$_2$CF$_3$ | CH | CH | CH | CH | N—CH$_3$ |
| 3.008 | SO | —CH$_2$CH$_3$ | S | CF$_2$CF$_3$ | CH | CH | CH | CH | N—CH$_3$ |
| 3.009 | SO$_2$ | —CH$_2$CH$_3$ | S | CF$_2$CF$_3$ | CH | CH | CH | CH | N—CH$_3$ |
| 3.010 | S | —CH$_2$CH$_3$ | S | CF$_3$ | CH | CH | C—CF$_3$ | CH | N—CH$_3$ |
| 3.011 | SO | —CH$_2$CH$_3$ | S | CF$_3$ | CH | CH | C—CF$_3$ | CH | N—CH$_3$ |
| 3.012 | SO$_2$ | —CH$_2$CH$_3$ | S | CF$_3$ | CH | CH | C—CF$_3$ | CH | N—CH$_3$ |
| 3.013 | S | —CH$_2$CH$_3$ | S | —SCF$_3$ | CH | CH | C—CF$_3$ | CH | N—CH$_3$ |
| 3.014 | SO | —CH$_2$CH$_3$ | S | —SCF$_3$ | CH | CH | C—CF$_3$ | CH | N—CH$_3$ |
| 3.015 | SO$_2$ | —CH$_2$CH$_3$ | S | —SCF$_3$ | CH | CH | C—CF$_3$ | CH | N—CH$_3$ |
| 3.016 | S | —CH$_2$CH$_3$ | S | CF$_2$CF$_3$ | CH | CH | C—CF$_3$ | CH | N—CH$_3$ |
| 3.017 | SO | —CH$_2$CH$_3$ | S | CF$_2$CF$_3$ | CH | CH | C—CF$_3$ | CH | N—CH$_3$ |
| 3.018 | SO$_2$ | —CH$_2$CH$_3$ | S | CF$_2$CF$_3$ | CH | CH | C—CF$_3$ | CH | N—CH$_3$ |
| 3.019 | S | —CH$_2$CH$_3$ | S | CF$_3$ | CH | C—CF$_3$ | CH | CH | N—CH$_3$ |

TABLE 3-continued

| Comp. No. | X | $R_1$ | $A_1$ | $R_2$ | $A_2$ | $A_3$ | $A_4$ | $A_5$ | $G_3$ |
|---|---|---|---|---|---|---|---|---|---|
| 3.020 | SO | —$CH_2CH_3$ | S | $CF_3$ | CH | C—$CF_3$ | CH | CH | N—$CH_3$ |
| 3.021 | $SO_2$ | —$CH_2CH_3$ | S | $CF_3$ | CH | C—$CF_3$ | CH | CH | N—$CH_3$ |
| 3.022 | S | —$CH_2CH_3$ | S | —$SCF_3$ | CH | C—$CF_3$ | CH | CH | N—$CH_3$ |
| 3.023 | SO | —$CH_2CH_3$ | S | —$SCF_3$ | CH | C—$CF_3$ | CH | CH | N—$CH_3$ |
| 3.024 | $SO_2$ | —$CH_2CH_3$ | S | —$SCF_3$ | CH | C—$CF_3$ | CH | CH | N—$CH_3$ |
| 3.025 | S | —$CH_2CH_3$ | S | $CF_2CF_3$ | CH | C—$CF_3$ | CH | CH | N—$CH_3$ |
| 3.026 | SO | —$CH_2CH_3$ | S | $CF_2CF_3$ | CH | C—$CF_3$ | CH | CH | N—$CH_3$ |
| 3.027 | $SO_2$ | —$CH_2CH_3$ | S | $CF_2CF_3$ | CH | C—$CF_3$ | CH | CH | N—$CH_3$ | and the N-oxides and tautomers of the compounds of Table 3.

Table 4:

This table discloses the 128 compounds of the formula I-1d:

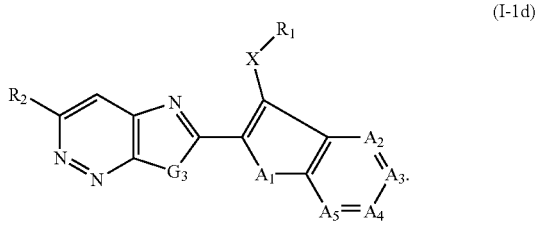

(I-1d)

TABLE 4

| Comp. No. | X | $R_1$ | $A_1$ | $R_2$ | $A_2$ | $A_3$ | $A_4$ | $A_5$ | $G_3$ |
|---|---|---|---|---|---|---|---|---|---|
| 4.001 | S | —$CH_2CH_3$ | S | $CF_3$ | CH | CH | CH | CH | N—$CH_3$ |
| 4.002 | SO | —$CH_2CH_3$ | S | $CF_3$ | CH | CH | CH | CH | N—$CH_3$ |
| 4.003 | $SO_2$ | —$CH_2CH_3$ | S | $CF_3$ | CH | CH | CH | CH | N—$CH_3$ |
| 4.004 | S | —$CH_2CH_3$ | S | —$SCF_3$ | CH | CH | CH | CH | N—$CH_3$ |
| 4.005 | SO | —$CH_2CH_3$ | S | —$SCF_3$ | CH | CH | CH | CH | N—$CH_3$ |
| 4.006 | $SO_2$ | —$CH_2CH_3$ | S | —$SCF_3$ | CH | CH | CH | CH | N—$CH_3$ |
| 4.007 | S | —$CH_2CH_3$ | S | $CF_2CF_3$ | CH | CH | CH | CH | N—$CH_3$ |
| 4.008 | SO | —$CH_2CH_3$ | S | $CF_2CF_3$ | CH | CH | CH | CH | N—$CH_3$ |
| 4.009 | $SO_2$ | —$CH_2CH_3$ | S | $CF_2CF_3$ | CH | CH | CH | CH | N—$CH_3$ |
| 4.010 | S | —$CH_2CH_3$ | S | $CF_3$ | CH | CH | C—$CF_3$ | CH | N—$CH_3$ |
| 4.011 | SO | —$CH_2CH_3$ | S | $CF_3$ | CH | CH | C—$CF_3$ | CH | N—$CH_3$ |
| 4.012 | $SO_2$ | —$CH_2CH_3$ | S | $CF_3$ | CH | CH | C—$CF_3$ | CH | N—$CH_3$ |
| 4.013 | S | —$CH_2CH_3$ | S | —$SCF_3$ | CH | CH | C—$CF_3$ | CH | N—$CH_3$ |
| 4.014 | SO | —$CH_2CH_3$ | S | —$SCF_3$ | CH | CH | C—$CF_3$ | CH | N—$CH_3$ |
| 4.015 | $SO_2$ | —$CH_2CH_3$ | S | —$SCF_3$ | CH | CH | C—$CF_3$ | CH | N—$CH_3$ |
| 4.016 | S | —$CH_2CH_3$ | S | $CF_2CF_3$ | CH | CH | C—$CF_3$ | CH | N—$CH_3$ |
| 4.017 | SO | —$CH_2CH_3$ | S | $CF_2CF_3$ | CH | CH | C—$CF_3$ | CH | N—$CH_3$ |
| 4.018 | $SO_2$ | —$CH_2CH_3$ | S | $CF_2CF_3$ | CH | CH | C—$CF_3$ | CH | N—$CH_3$ |
| 4.019 | S | —$CH_2CH_3$ | S | $CF_3$ | CH | C—$CF_3$ | CH | CH | N—$CH_3$ |
| 4.020 | SO | —$CH_2CH_3$ | S | $CF_3$ | CH | C—$CF_3$ | CH | CH | N—$CH_3$ |
| 4.021 | $SO_2$ | —$CH_2CH_3$ | S | $CF_3$ | CH | C—$CF_3$ | CH | CH | N—$CH_3$ |
| 4.022 | S | —$CH_2CH_3$ | S | —$SCF_3$ | CH | C—$CF_3$ | CH | CH | N—$CH_3$ |
| 4.023 | SO | —$CH_2CH_3$ | S | —$SCF_3$ | CH | C—$CF_3$ | CH | CH | N—$CH_3$ |
| 4.024 | $SO_2$ | —$CH_2CH_3$ | S | —$SCF_3$ | CH | C—$CF_3$ | CH | CH | N—$CH_3$ |
| 4.025 | S | —$CH_2CH_3$ | S | $CF_2CF_3$ | CH | C—$CF_3$ | CH | CH | N—$CH_3$ |
| 4.026 | SO | —$CH_2CH_3$ | S | $CF_2CF_3$ | CH | C—$CF_3$ | CH | CH | N—$CH_3$ |
| 4.027 | $SO_2$ | —$CH_2CH_3$ | S | $CF_2CF_3$ | CH | C—$CF_3$ | CH | CH | N—$CH_3$ | and the N-oxides and tautomers of the compounds of Table 4.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp., *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtil is*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp., *Brachycaudus* spp, *Brevicoryne brassicae*, *Cacopsylla* spp, *Cavariella aegopodii Scop.*, *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp., *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp., *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp., *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp., *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp., *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; *Needle nematodes, Longidorus elongatus* and other *Longidorus* species; *Pin nematodes, Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus* prim itivus and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; Deroceras (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae *Helicigona arbustorum*); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO 2005/113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables AA and BB:

TABLE AA

Examples of exotic woodborers of economic importance.

| Family | Species | Host or Crop Infested |
|---|---|---|
| Buprestidae | Agrilus planipennis | Ash |
| Cerambycidae | Anoplura glabripennis | Hardwoods |
| Scolytidae | Xylosandrus crassiusculus | Hardwoods |
| | X. mutilatus | Hardwoods |
| | Tomicus piniperda | Conifers |

TABLE BB

Examples of native woodborers of economic importance.

| Family | Species | Host or Crop Infested |
|---|---|---|
| Buprestidae | Agrilus anxius | Birch |
| | Agrilus politus | Willow, Maple |
| | Agrilus sayi | Bayberry, Sweetfern |
| | Agrilus vittaticolllis | Apple, Pear, Cranberry, Serviceberry, Hawthorn |
| | Chrysobothris femorata | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | Texania campestris | Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |

TABLE BB-continued

Examples of native woodborers of economic importance.

| Family | Species | Host or Crop Infested |
| --- | --- | --- |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworrn, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and green bugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas* taignus and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unepodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g. tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):

| Emulsifiable concentrates: | |
|---|---|
| active ingredient: | 1 to 95%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 5 to 75%, preferably 10 to 50% |
| surfactant: | 94 to 24%, preferably 88 to 30% |
| solid carrier: | 1 to 40%, preferably 2 to 30% |
| Granulates: | |
| active ingredient: | 0.5 to 30%, preferably 3 to 15% |
| solid carrier: | 99.5 to 70%, preferably 97 to 85% |

PREPARATORY EXAMPLES

"Mp" means melting point in ° C. Free radicals represent methyl groups. $^1$H and $^{19}$F NMR measurements were recorded on Brucker 400 MHz or 300 MHz spectrometers, chemical shifts are given in ppm relevant to a TMS standard. Spectra measured in deuterated solvents as indicated.
LCMS Methods:
Method A (SQD13):
Spectra were recorded on a Mass Spectrometer from Waters (SQD Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Synthesis

Intermediate 1: Synthesis of 3-ethylsulfanylbenzothiophene-2-carboxylic Acid

Step A: methyl 3-ethylsulfanylbenzothiophene-2-carboxylate

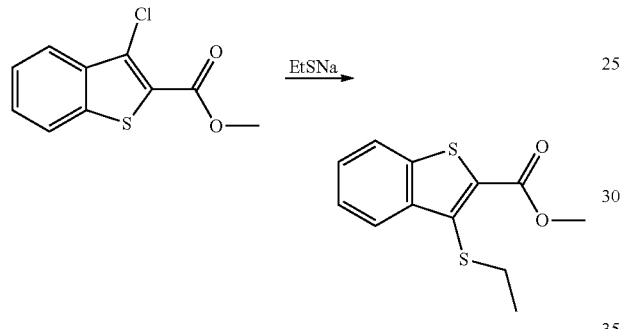

To stirred solution of methyl 3-chlorobenzothiophene-2-carboxylate (commercially available, 1 g) in N,N-dimethylformamide (8.61 mL) was added sodium ethanethiolate (0.506 g, 1 eq.). The reaction mixture was stirred at ambient temperature for 2 hours. Then 0.25 eq. of sodium ethanethiolate was added. The reaction was monitored by TLC. After completion of the starting material, the reaction mixture was diluted with water and extracted with ethyl acetate (2×). Organic layers were combinated and dried over Na$_2$SO$_4$. Filtered, concentrated and purified by column chromatography using cyclohexane-ethyl acetate to give the desired compound (0.92 g; Yield=85%). $^1$H NMR (400 MHz, CDCl$_3$): δ (ppm) 8.20 (m, 1H), 7.82 (m, 1H), 7.48 (m, 2H), 3.97 (s, 3H), 3.04 (q, 2H), 1.20 (t, 3H).

Step B: 3-ethylsulfanylbenzothiophene-2-carboxylic Acid

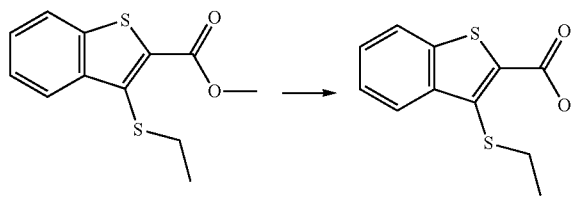 [SMILES: CCSc1c(C(=O)OC)sc2ccccc12 ; CCSc1c(C(=O)O)sc2ccccc12]

To as stirred solution of methyl 3-ethylsulfanylbenzothiophene-2-carboxylate (0.9 g) in a mixture of THF (14.3 ml) and water (3.57 mL) was added lithium hydroxide monohydrate (1.1 equiv., 0.094 g) at ambient temperature. The reaction mixture was stirred for 2 hours at ambient temperature. The reaction was monitored by TLC. After completion of the starting material, reaction mixture was acidified with hydrogen chloride (1N) and extracted with ethyl acetate (2). Organic layers were combinated and dried over Na$_2$SO$_4$. Filtered, concentrated under reduced pressure to give the crude solid, which was used without purification for the next step (804 mg, 94.62% Yield). $^1$H NMR (400 MHz, DMSO-d$_6$): δ (ppm) 8.10 (m, 2H), 7.57 (m, 2H), 3.04 (q, 2H), 1.10 (t, 3H).

Example A1 and A2: Preparation of 2-(3-ethylsulfonylbenzothiophen-2-yl)-3-methyl-6-(trifluoromethyl)imidazo [4,5-b] pyridine (A2, 1.002) and 2-(3-ethylsulfanylbenzothiophen-2-yl)-3-methyl-6-(trifluoromethyl)imidazo[4,5-b]pyridine (A1, 1.001)

Step A: Preparation of 3-ethylsulfanyl-N-[2-(methylamino)-5-(trifluoromethyl)-3-pyridyl]benzothiophene-2-carboxamide and N-[3-amino-5-(trifluoromethyl)-2-pyridyl]-3-ethylsulfanyl-N-methyl-benzothiophene-2-carboxamide

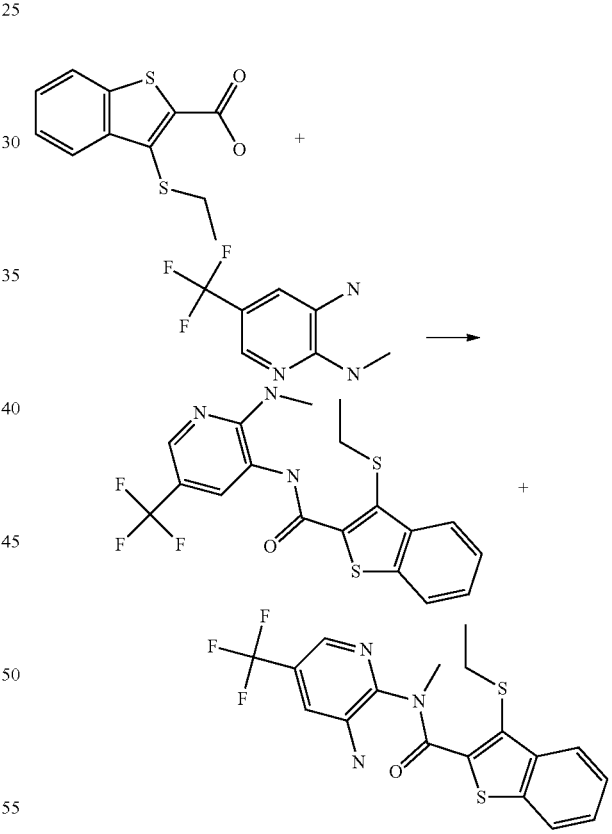

To a suspension of 3-ethylsulfanylbenzothiophene-2-carboxylic acid (Intermediate 1, 0.26 g) in dichloromethane (2 ml) was added one drop of N,N-dimethylformamide, followed by oxalyl chloride (2.5 equiv., 0.2177 mL, 0.317 g). After the end of gas evolution, the reaction mixture was in the form of a pale yellow solution. The latter was evaporated under reduced pressure at a bath temperature of 60° C. The residue formed dark red crystals of 5-bromo-3-ethylsulfanyl-pyridine-2-carbonyl chloride and the residue was redissolved in 6 ml of THF.

To a solution of N2-methyl-5-(trifluoromethyl)pyridine-2,3-diamine (commercially available: CAS 172648-55-4, 187 mg) in ethyl acetate (2 ml) was added N,N-diethylethanamine (2.5 equiv., 0.344 mL, 0.25 g) then The resulting solution was cooled with an ice bath, before slow addition of the previous acyl chloride solution. The resulting mixture was stirred 2 hour at 0° C. The solution was neutralized by addition of a saturated aqueous solution of sodium bicarbonate and the product was extracted twice with ethyl acetate. The organic solution was dried over sodium sulfate and evaporated under reduced pressure to yield the crude product. a mixture of 3-ethylsulfanyl-N-[2-(methylamino)-5-(trifluoromethyl)-3-pyridyl]benzothiophene-2-carboxamide and N-[3-amino-5-(trifluoromethyl)-2-pyridyl]-3-ethylsulfanyl-N-methyl-benzothiophene-2-carboxamide was obtained after column chromatography over silica gel, eluting with ethyl acetate/cyclohexane and used without extra purification. LC-MS (Method A): RT 1.16 (412, MH+)

A mixture of 3-ethylsulfanyl-N-[5-(methylamino)-2-(trifluoromethyl)-4-pyridyl]benzothiophene-2-carboxamide and N-[4-amino-6-(trifluoromethyl)-3-pyridyl]-3-ethylsulfanyl-N-methyl-benzothiophene-2-carboxamide (as described in the following scheme) were synthesised using the same protocol and N-3-methyl-6-(trifluoromethyl)pyridine-3,4-diamine as starting material (prepared as described in WO15000715). LC-MS (Method A): RT 0.99 (412, MH+)

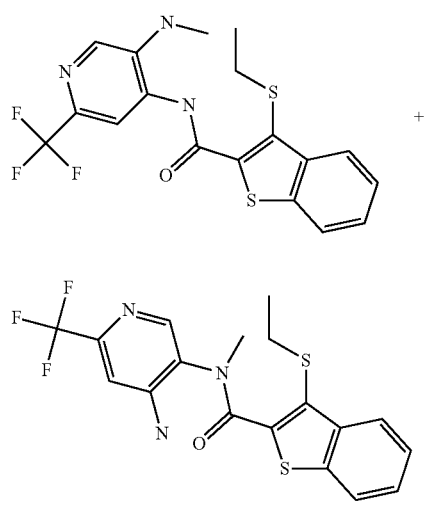

+

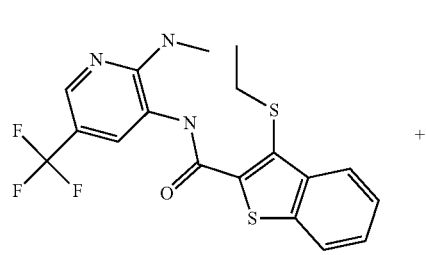

Step B: Preparation of 2-(3-ethylsulfanylbenzothiophen-2-yl)-3-methyl-6-(trifluoromethyl)imidazo[4,5-b]pyridine A1

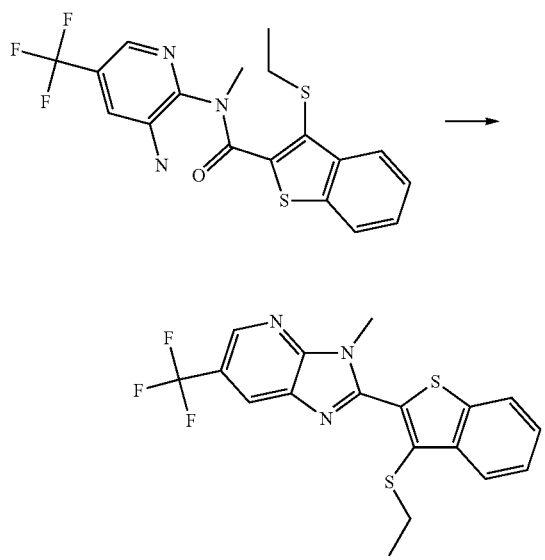

A mixture of 3-ethylsulfanyl-N-[2-(methylamino)-5-(trifluoromethyl)-3-pyridyl]benzothiophene-2-carboxamide and N-[3-amino-5-(trifluoromethyl)-2-pyridyl]-3-ethylsulfanyl-N-methyl-benzothiophene-2-carboxamide (0.23 g) in acetic acid (2.5 ml) was heated to 150° C. for 30 minutes in a microwave. The reaction was monitored by TLC. After completion of the starting material, reaction mixture was diluted with ethyl acetate and washed with water. Organic layer was dried over Na$_2$SO$_4$. Filtered, concentrated and purified by column chromatography using cyclohexane-ethyl acetate to give the desired compound as a white solid (112 mg; Yield=58.6%). $^1$H NMR (400 MHz, CDCl$_3$): δ (ppm) 8.75 (s, 1H), 8.36 (s, 1H), 8.13 (d, 1H), 7.94 (d, 1H), 7.54 (m, 2H), 3.94 (s, 3H), 2.68 (q, 2H), 1.04 (t, 3H).

Compound 2-(3-ethylsulfanylbenzothiophen-2-yl)-1-methyl-6-(trifluoromethyl)imidazo[4,5-c]pyridine B1 (2.001) was synthesised using the same procedure and as stating material, a mixture of 3-ethylsulfanyl-N-[5-(methylamino)-2-(trifluoromethyl)-4-pyridyl]benzothiophene-2-carboxamide and N-[4-amino-6-(trifluoromethyl)-3-pyridyl]-3-ethylsulfanyl-N-methyl-benzothiophene-2-carboxamide prepared before.

Step C: Preparation of 2-(3-ethylsulfonylbenzothiophen-2-yl)-3-methyl-6-(trifluoromethyl)imidazo [4,5-b] pyridine A2

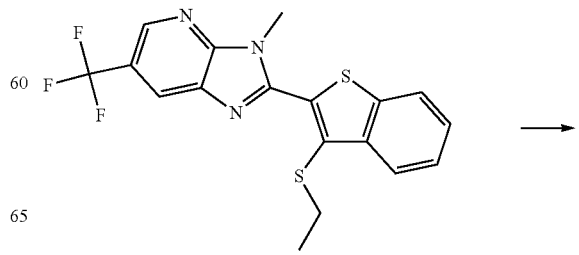

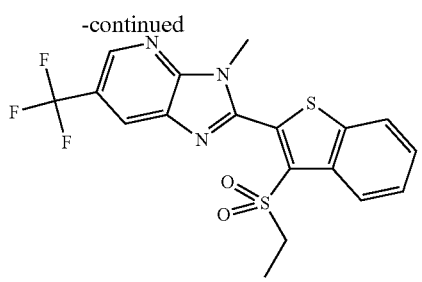

To a stirred solution of compound of 2-(3-ethylsulfanyl-benzothiophen-2-yl)-3-methyl-6-(trifluoromethyl)imidazo[4,5-b]pyridine (A1, 1.001, 0.112 g) in CH$_2$Cl$_2$ (12 ml) was added m-CPBA (2.3 equiv., 0.1614 g) at ambient temperature. The reaction mixture was then stirred for 1 hour. The reaction was monitored by TLC. After completion of the starting, the reaction mixture was quenched with saturated Na$_2$S$_2$O$_3$, NaHCO$_3$ and extracted with CH$_2$Cl$_2$ (2×). CH$_2$Cl$_2$ layer was dried over Na2SO4. Filtered, concentrated and the crude was purified by column chromatography using cyclohexane-ethyl acetate to give the desired compound as a white solid (41 mg; Yield=34%). $^1$H NMR (400 MHz, CDCl$_3$): δ (ppm) 8.78 (s, 1H), 8.52 (d, 1H), 8.34 (s, 1H), 7.98 (d, 1H), 7.64 (m, 2H), 3.88 (s, 3H), 3.34 (q, 2H), 1.28 (t, 3H).

2-(3-ethylsulfonylbenzothiophen-2-yl)-1-methyl-6-(trifluoromethyl)imidazo[4,5-c]pyridine B2 (2.002) was synthesised using the same procedure and as stating material, Compound 2-(3-ethylsulfanylbenzothiophen-2-yl)-1-methyl-6-(trifluoromethyl)imidazo[4,5-c]pyridine B1 (2.001) prepared before. LC-MS (Method A) RT 1.11 394.5 (MH$^+$).

Example A3: 2-(6-bromo-3-ethylsulfanyl-benzothiophen-2-yl)-3-methyl-6-(trifluoromethylsulfanyl)imidazo[4,5-b]pyridine A3

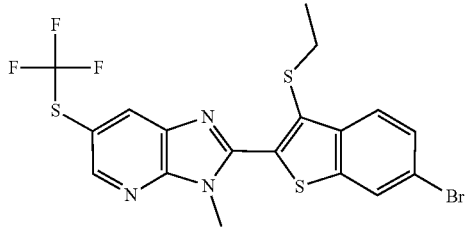

A3

Step A: 6-bromo-3-ethylsulfanyl-benzothiophene-2-carboxylic Acid

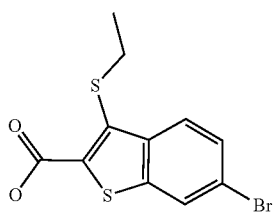 [SMILES: CCSc1c(C(=O)O)sc2cc(Br)ccc12]

To stirred solution of 6-bromo-3-chloro-benzothiophene-2-carboxylic acid (commercially available, 7.3 g) in N,N-dimethylformamide (50 mL) was added sodium ethanethiolate (2 eq.). The reaction mixture was stirred at 100° C. for 1.5 hours. The reaction was monitored by TLC. After completion of the starting material, the reaction mixture was diluted with water and extracted with ethyl acetate (2×). Organic layers were combinated and dried over sodium sulphate, filtered, concentrated and purified by column chromatography using cyclohexane-ethyl acetate to give the desired compound (0.92 g; Yield=39%). $^1$H NMR (400 MHz, CDCl3) δ ppm 1.29 (t, 3H), 3.01 (q, 2H), 7.66 (dd, 1H), 7.96 (d, 1H), 8.11 (d, 1H).

Step B: 6-bromo-3-ethylsulfanyl-N-[2-(methylamino)-5-(trifluoromethylsulfanyl)-3-pyridyl]benzothiophene-2-carboxamide and N-[3-amino-5-(trifluoromethylsulfanyl)-2-pyridyl]-6-bromo-3-ethylsulfanyl-N-methyl-benzothiophene-2-carboxamide

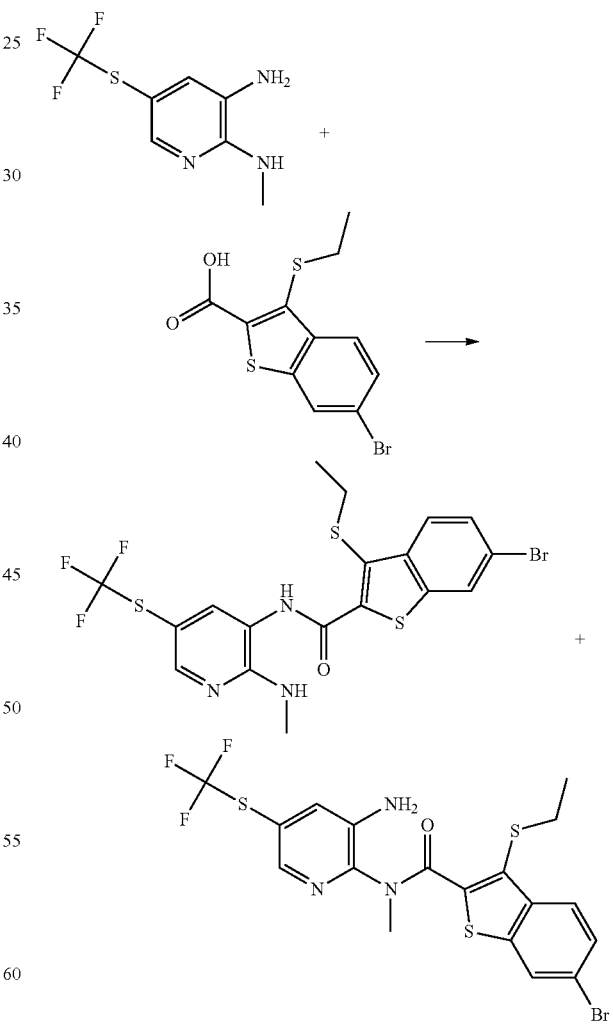

To a suspension of 6-bromo-3-ethylsulfanyl-benzothiophene-2-carboxylic acid (Prepared in Step A, 213 mg) in dichloromethane (5 ml) was added one drop of N,N-dimethylformamide, followed by oxalyl chloride (2.5 equiv., 0.107 mL). After the end of gas evolution, the reaction mixture was in the form of a pale yellow solution. The latter was evaporated under reduced pressure at a bath temperature of 60° C. The residue formed dark red crystals of 5-bromo-5-bromo-3-ethylsulfanyl-benzothiophene-2-carboxylic chloride and the residue was redissolved in 6 ml of THF.

To a solution of N2-methyl-5-(trifluoromethylsulfanyl) pyridine-2,3-diamine (commercially available CAS 1383840-73-0,150 mg) in ethyl acetate (2 ml) was added N,N-diethylethanamine (2.5 equiv., 0.237 mL) then the resulting solution was cooled with an ice bath, before slow addition of the previous acyl chloride solution. The resulting mixture was stirred 1 hour at room temperature. The solution was neutralized by addition of a saturated aqueous solution of sodium bicarbonate and the product was extracted twice with ethyl acetate. The organic solution was dried over sodium sulfate and evaporated under reduced pressure to yield the crude product. a mixture of 6-bromo-3-ethylsulfanyl-N-[2-(methylamino)-5-(trifluoromethylsulfanyl)-3-pyridyl]benzothiophene-2-carboxamide and N-[3-amino-5-(trifluoromethylsulfanyl)-2-pyridyl]-6-bromo-3-ethylsulfanyl-N-methyl-benzothiophene-2-carboxamide was obtained after column chromatography over silica gel, eluting with ethyl acetate/cyclohexane and used without extra purification. LC-MS (Method A): RT 1.32 522 (M+H⁻), 524 (M+H⁺).

Step C: 2-(6-bromo-3-ethylsulfanyl-benzothiophen-2-yl)-3-methyl-6-(trifluoromethyl)imidazo[4,5-b]pyridine A3

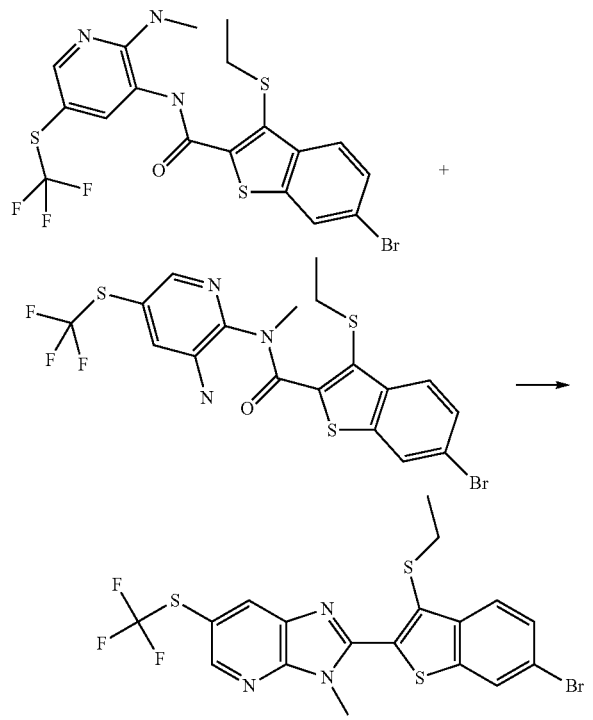

A mixture of 6-bromo-3-ethylsulfanyl-N-[2-(methylamino)-5-(trifluoromethylsulfanyl)-3-pyridyl]benzothiophene-2-carboxamide and N-[3-amino-5-(trifluoromethylsulfanyl)-2-pyridyl]-6-bromo-3-ethylsulfanyl-N-methyl-benzothiophene-2-carboxamide (0.32 g) in acetic acid (4 ml) was heated to 150° C. for 30 minutes in a microwave. The reaction was monitored by TLC. After completion of the starting material, reaction mixture was diluted with ethyl acetate and washed with water. Organic layer was dried over Na₂SO₄. Filtered, concentrated and purified by column chromatography using cyclohexane-ethyl acetate to give the Example A3 as a white solid (310 mg; Yield=100%). ¹H NMR (400 MHz, CDCl₃) δ ppm 1.04 (t, 3H), 2.68 (q, 2H), 3.93 (s, 3H) 7.66 (dd, 1H), 7.98 (d, 1H), 8.09 (d, 1H), 8.43 (d, 1H), 8.70 (d, 1H). LC-MS (Method A): RT 1.37 (506, MH+).

Example A4: 2-(6-bromo-3-ethylsulfonyl-benzothiophen-2-yl)-3-methyl-6-(trifluoromethyl)imidazo[4,5-b]pyridine

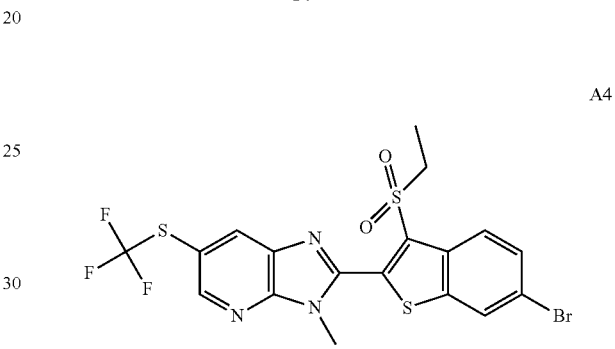

Step A: Preparation of 2-(6-bromo-3-ethylsulfonyl-benzothiophen-2-yl)-3-methyl-6-(trifluoromethylsulfanyl)imidazo[4,5-b]pyridine A4

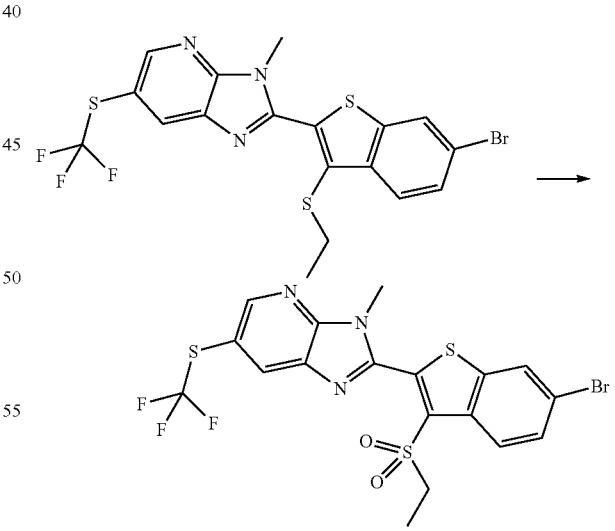

To a stirred solution of compound of 2-(6-bromo-3-ethylsulfanyl-benzothiophen-2-yl)-3-methyl-6-(trifluoromethylsulfanyl)imidazo[4,5-b]pyridine (Example A3, 310 mg) in CH₂Cl₂ (20 ml) was added m-CPBA (2.05 equiv., 290 mg) at ambient temperature. The reaction mixture was then stirred for 1 hour. The reaction was monitored by TLC.

After completion of the starting, the reaction mixture was quenched with saturated Na₂S₂O₃, NaHCO₃ and extracted with CH₂Cl₂ (2×). the combined organic layers were dried over sodium sulfate, filtered, concentrated and the crude was purified by column chromatography using cyclohexane-ethyl acetate to give the desired compound as a white solid (310 mg; Yield=94%). ¹H NMR (400 MHz, CDCl₃) δ ppm 1.30 (t, 4H), 3.34 (q, 2H), 3.86 (s, 3H), 7.75 (dd, 1H), 8.15 (d, 1H), 8.40 (m, 2H), 8.71 (d, 1H).

Example A5: 2-[3-ethylsulfanyl-6-(trifluoromethyl)benzothiophen-2-yl]-3-methyl-6-(trifluoromethyl)imidazo[4,5-b]pyridine Step A: Synthesis of 3-ethylsulfanyl-6-(trifluoromethyl)benzothiophene-2-carboxylic Acid Step B: 3-ethylsulfanyl-N-[2-(methylamino)-5-(trifluoromethyl)-3-pyridyl]-6-(trifluoromethyl)benzothiophene-2-carboxamide and N-[3-amino-5-(trifluoromethyl)-2-pyridyl]-3-ethylsulfanyl-N-methyl-6-(trifluoromethyl)benzothiophene-2-carboxamide

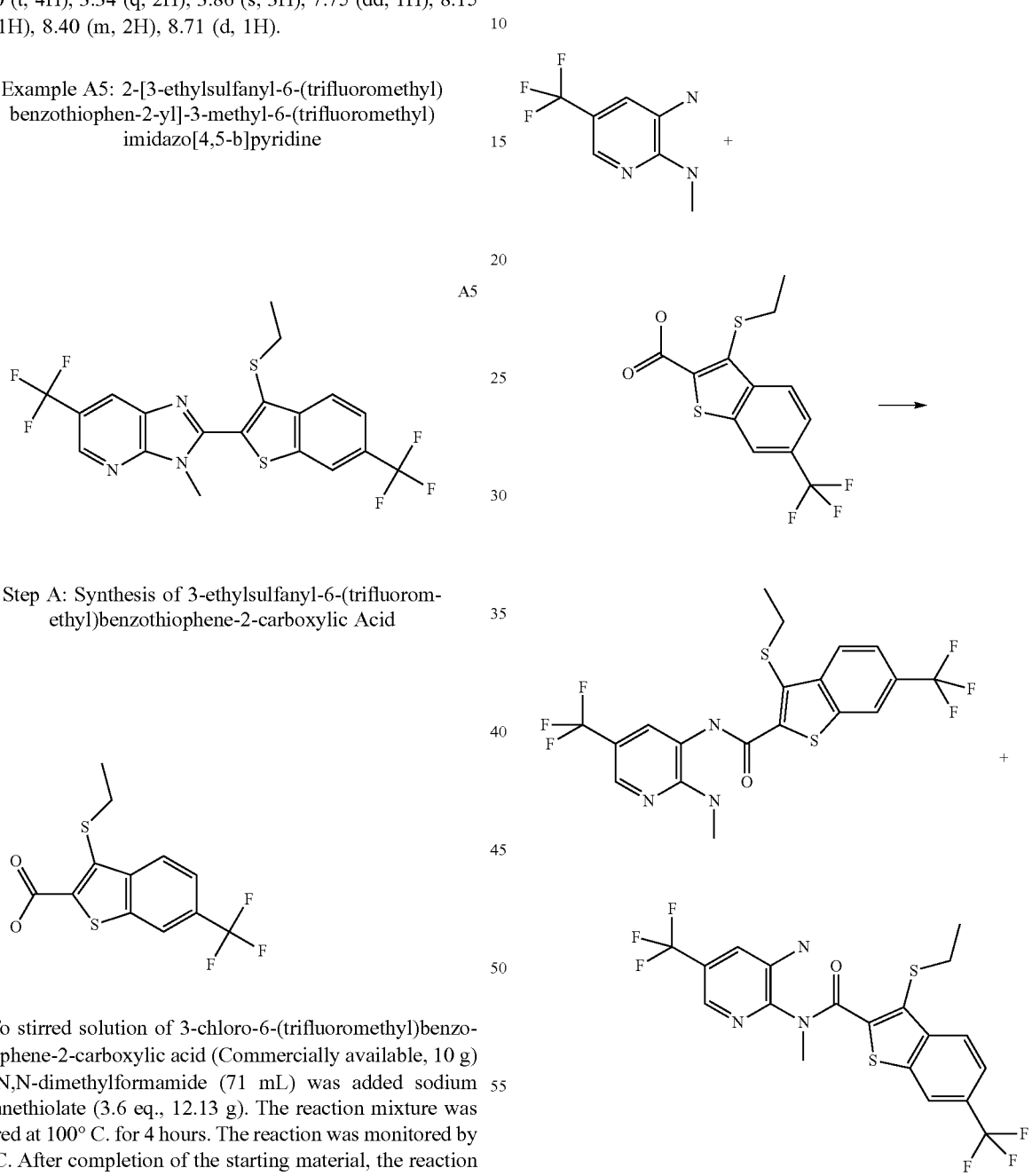

To stirred solution of 3-chloro-6-(trifluoromethyl)benzothiophene-2-carboxylic acid (Commercially available, 10 g) in N,N-dimethylformamide (71 mL) was added sodium ethanethiolate (3.6 eq., 12.13 g). The reaction mixture was stirred at 100° C. for 4 hours. The reaction was monitored by TLC. After completion of the starting material, the reaction mixture was diluted with water and extracted with ethyl acetate (2×). Organic layers were combined and dried over Na₂SO₄, filtered, concentrated and the crude was purified by column chromatography using cyclohexane-ethyl acetate to give the desired compound (4.21 g; Yield=38%). ¹H NMR (400 MHz, DMSO) δ ppm 1.08 (t, 3H), 3 (m, 2H), 7.84 (dd, 1H), 7.96 (s, 1H), 8.3 (m, 1H), 8.64 (s, 1H), 13.95 (s, 1H). LC-MS (Method A): RT 1.08 (307, MH+).

Prepared from N2-methyl-5-(trifluoromethylsulfanyl)pyridine-2,3-diamine (Commercially available, Cas: 172648-55-4) and 3-ethylsulfanyl-6-(trifluoromethyl)benzothiophene-2-carboxylic acid, using a similar protocol as described in Example A3 Step B. LC-MS (Method A) RT 1.26, 478 (MH−) 481 (MH+).

Step C Example A5: Preparation of 2-(6-bromo-3-ethylsulfonyl-benzothiophen-2-yl)-3-methyl-6-(trifluoromethylsulfanyl)imidazo[4,5-b]pyridine A5

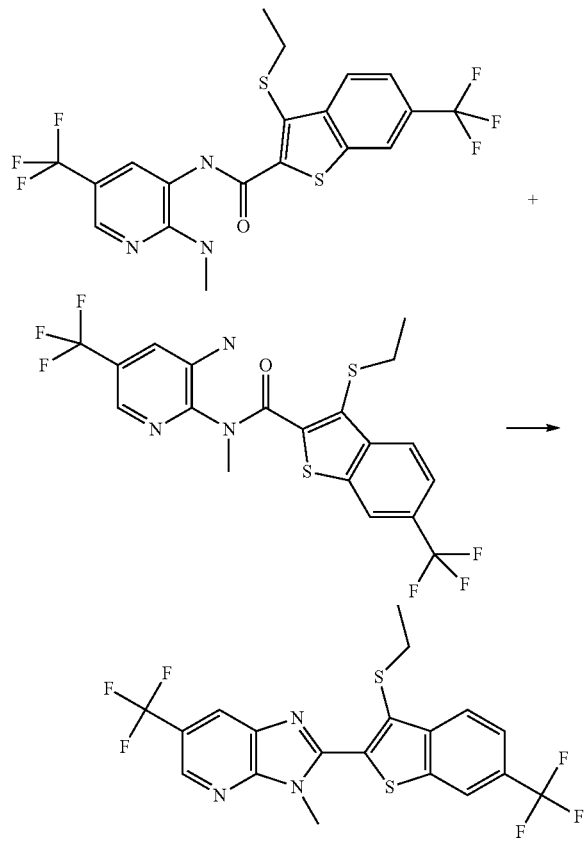

Prepared from 3-ethylsulfanyl-N-[2-(methylamino)-5-(trifluoromethyl)-3-pyridyl]-6-(trifluoromethyl)benzothiophene-2-carboxamide and N-[3-amino-5-(trifluoromethyl)-2-pyridyl]-3-ethylsulfanyl-N-methyl-6-(trifluoromethyl)benzothiophene-2-carboxamide, using a similar protocol as described in Example A3 (step C). LC-MS (Method A) RT 1.31, 462 (MH−). ¹H NMR (400 MHz, CDCl3) δ ppm 1.05 (t, 3H), 2.69 (q, 2H), 3.96 (s, 3H), 7.80 (m, 1H), 8.27 (m, 2H), 8.38 (m, 1H), 8.79 (m, 1H).

Example A6: 2-[3-ethylsulfonyl-6-(trifluoromethyl)benzothiophen-2-yl]-3-methyl-6-(trifluoromethyl)imidazo[4,5-b]pyridine

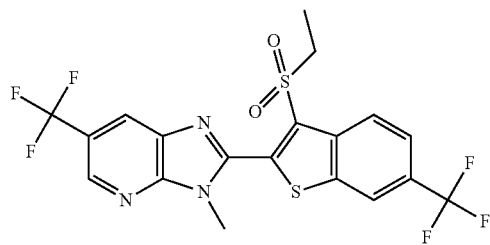

A6

Prepared from Example A5, using a similar protocol as described in Example A4 (Step A). LC-MS (Method A) RT 1.13, 492 (MH−) 495 (MH+). ¹H NMR (400 MHz, CDCl3) δ ppm 1.32 (t, 3H), 3.38 (q, 2H), 3.89 (s, 3H), 7.88 (m, 1H), 8.30 (s, 1H), 8.35 (m, 1H) 8.68 (m, 1H), 8.78 (m, 1H).

Example A7: 2-(6-bromo-3-ethylsulfanyl-benzothiophen-2-yl)-3-methyl-6-(trifluoromethyl)imidazo[4,5-b]pyridine

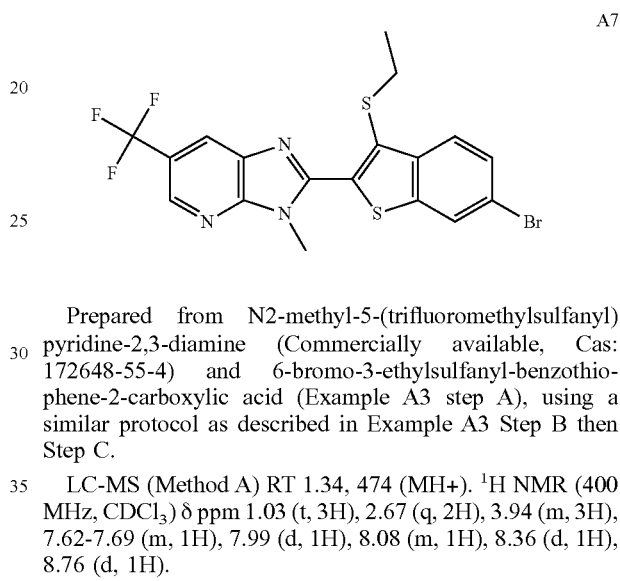

A7

Prepared from N2-methyl-5-(trifluoromethylsulfanyl)pyridine-2,3-diamine (Commercially available, Cas: 172648-55-4) and 6-bromo-3-ethylsulfanyl-benzothiophene-2-carboxylic acid (Example A3 step A), using a similar protocol as described in Example A3 Step B then Step C.

LC-MS (Method A) RT 1.34, 474 (MH+). ¹H NMR (400 MHz, CDCl₃) δ ppm 1.03 (t, 3H), 2.67 (q, 2H), 3.94 (m, 3H), 7.62-7.69 (m, 1H), 7.99 (d, 1H), 8.08 (m, 1H), 8.36 (d, 1H), 8.76 (d, 1H).

Example A8: 2-(6-bromo-3-ethylsulfonyl-benzothiophen-2-yl)-3-methyl-6-(trifluoromethyl)imidazo[4,5-b]pyridine

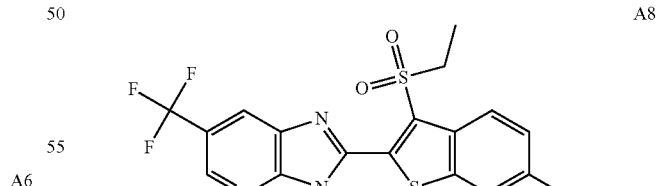

A8

Prepared from 2-(6-bromo-3-ethylsulfanyl-benzothiophen-2-yl)-3-methyl-6-(trifluoromethyl)imidazo[4,5-b]pyridine A7, using a similar protocol as described for Example A4 (Step A). LC-MS (Method A) RT 1.17, 506 (MH+). ¹H NMR (400 MHz, CDCl₃) δ ppm 1.30 (t, 3H), 3.34 (q, 2H), 3.88 (s, 3H), 7.75 (dd, 1H) 8.15 (d, 1H), 8.34 (d, 1H), 8.41 (d, 1H), 8.78 (d, 1H).

Example A9: 2-[3-ethylsulfonyl-6-[3-(trifluoromethyl)pyrazol-1-yl]benzothiophen-2-yl]-3-methyl-6-(trifluoromethyl)imidazo[4,5-b]pyridine A9

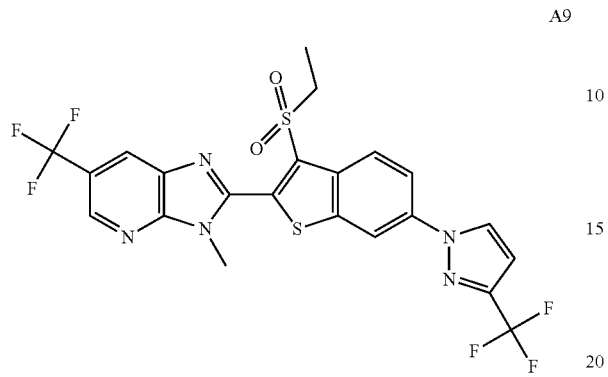

A9

A solution of 2-(6-bromo-3-ethylsulfonyl-benzothiophen-2-yl)-3-methyl-6-(trifluoromethyl)imidazo[4,5-b]pyridine A8 (0.200 g, 0.4 mmol), 3-(Trifluoromethyl)-1H-pyrazole (0.125 g, 0.912 mmol) in N,N-Dimethylformamide (5 mL) was degassed for 5 min with Argon, then Copper(I) iodide (0.0152 g, 0.079 mmol), N,N'-Dimethyl-ethylenediamine (0.0171 mL, 0.159 mmol) and Potassium carbonate (0.0443 g, 0.317 mmol) were added. The mixture was stirred overnight at 120° C., reaction was monitored by LC/MS. Water was added at the solution and the aqueous layer was extracted 3 times with ethyl acetate. The combined organic layer was washed 3 times with water, dried over sodium sulfate, filtered and evaporated under vacuum. The residue was purified by combi flash chromatography, using a gradient cyclohexane/ethyl acetate to give, after precipitation in cyclohexane, the title compound (0.018 g). LC-MS (Method A) RT 1.18, 561 (MH+). $^1$H NMR (400 MHz, CDCl$_3$) δ ppm 1.33 (t, 3H) 3.39 (q, 2H) 3.91 (s, 3H) 6.83 (d, 1H), 7.95 (dd, 1H) 8.12 (d, 1H) 8.35 (d, 1H), 8.46 (d, 1H), 8.66 (d, 1H) 8.79 (d, 1H).

Example A10: Preparation of 2-[3-ethylsulfonyl-6-(trifluoromethylsulfanyl)benzothiophen-2-yl]-3-methyl-6-(trifluoromethyl)imidazo[4,5-b]pyridine A10

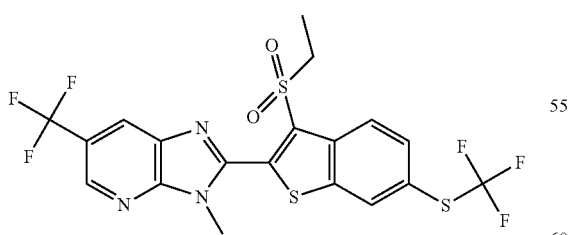

A10

A solution of 2-(6-bromo-3-ethylsulfonyl-benzothiophen-2-yl)-3-methyl-6-(trifluoromethyl)imidazo[4,5-b]pyridine A8 (0.200 g, 0.397 mmol) in acetonitrile (4.72 g, 6 mL, 115 mmol) was gassed with argon for 30 min. Then (bpy)CuSCF3 (0.384 g, 1.19 mmol) was added and the dark brown solution was refluxed for 20 hours (5% conversion according LC/MS). 6 equivalent more of (bpy)CuSCF3 were added and the reaction was refluxed over week end. Mixture reaction was allowed to cool to RT, was diluted with ethyl acetate and filtered through Hyflo to remove insoluble residue. The filtrate was concentrated under vacuum and residue was purified by Flash Chromatography to give 2-[3-ethylsulfonyl-6-(trifluoromethylsulfanyl)benzothiophen-2-yl]-3-methyl-6-(trifluoromethyl)imidazo[4,5-b]pyridine (0.07 g, 33.6% Yield). $^1$H NMR (400 MHz, CDCl$_3$) δ ppm 1.32 (t, 3H), 3.37 (q, 2H), 3.89 (s, 3H), 7.90 (m, 1H), 8.30 (m, 2H), 8.60 (d, 1H), 8.79 (s, 1H).

Example A11: Preparation of 2-(6-cyclopropyl-3-ethylsulfonyl-benzothiophen-2-yl)-3-methyl-6-(trifluoromethyl)imidazo[4,5-b]pyridine A11

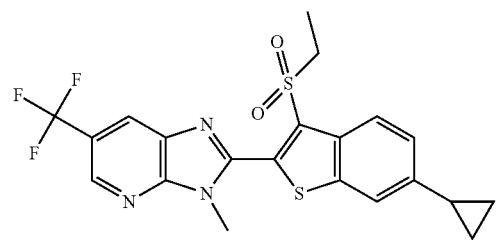

A11

To a solution of 2-(6-bromo-3-ethylsulfonyl-benzothiophen-2-yl)-3-methyl-6-(trifluoromethyl)imidazo[4,5-b]pyridine A8 (0.200 g, 0.397 mmol) in a mixture of toluene (3 mL, 28.1 mmol) and water (3 mL, 166.5 mmol) was added cyclopropylboronic acid (0.128 g, 1.43 mmol, 3.60), tetrakis(triphenylphosphine) palladium(0) (0.0459 g, 0.04 mmol) and potassium phosphate tribasic (0.521 g, 0.203 mL, 2.38 mmol). The mixture was then refluxed for 4 hours. After a complete conversion reaction mixture was extracted with ethyl acetate and water, organic layer was dried over sodium sulfate, filtered and evaporated under vacuum. The residue was purified by combi flash chromatography to give A11 (0.09 g, 0.19 mmol, 48.8% Yield). $^1$H NMR (400 MHz, CDCl$_3$) δ ppm 0.82-0.88 (m, 2H), 1.09-1.17 (m, 2H), 1.28 (t, 4H), 2.04-2.14 (m, 1H), 3.32 (q, 2H), 3.87 (s, 3H), 7.33 (dd, 1H), 7.67 (d, 1H), 8.33 (d, 1H), 8.37 (d, 1H), 8.76 (d, 1H). LC-MS (Method A) RT 1.22, 466 (MH+).

Example A12: Preparation of 2-[3-ethylsulfonyl-6-(1,1,2,2,2-pentafluoroethyl)benzothiophen-2-yl]-3-methyl-6-(trifluoromethyl)imidazo[4,5-b]pyridine A12

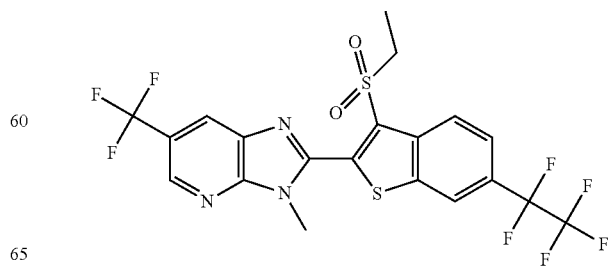

A12

In microwave vial purged with argon, 2-(6-bromo-3-ethylsulfonyl-benzothiophen-2-yl)-3-methyl-6-(trifluoromethyl)imidazo[4,5-b]pyridine A8 (0.200 g, 0.397 mmol) was dissolved in N-methyl-2-pyrrolidone (3 ml) and Pentafluoroethylator (0.303 g, 0.793 mmol). The vial was put in MW reactor at 90° C. for 2 hours. After a total conversion, water and ethyl acetate was added in the mixture, and then organic phase was dried on magnesium sulfate and concentrated on vacuum. The residue was purified by combi flash chromatography to give A12 (0.034 g, 0.06257 mmol, 15.8% Yield).
$^1$H NMR (400 MHz, CDCl$_3$) δ ppm 1.33 (t, 3H), 3.38 (q, 2H), 3.89 (s, 3H), 7.85 (d, 1H), 8.28 (s, 1H), 8.36 (d, 1H), 8.71 (d, 1H), 8.79 (d, 1H). LC-MS (Method A) RT 1.23, 544 (MH+).

Example B3: 2-[3-ethylsulfanyl-6-(trifluoromethyl)benzothiophen-2-yl]-3-methyl-6-(trifluoromethyl)imidazo[4,5-c]pyridine B3

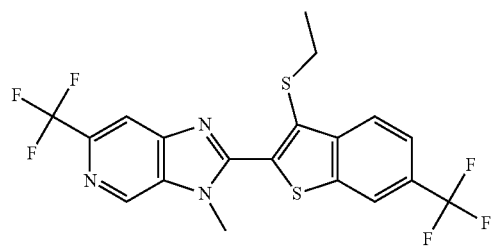

Step A: Synthesis of 3-ethylsulfanyl-N-[5-(methylamino)-2-(trifluoromethyl)-4-pyridyl]-6-(trifluoromethyl)benzothiophene-2-carboxamide and N-[4-amino-6-(trifluoromethyl)-3-pyridyl]-3-ethylsulfanyl-N-methyl-6-(trifluoromethyl)benzothiophene-2-carboxamide

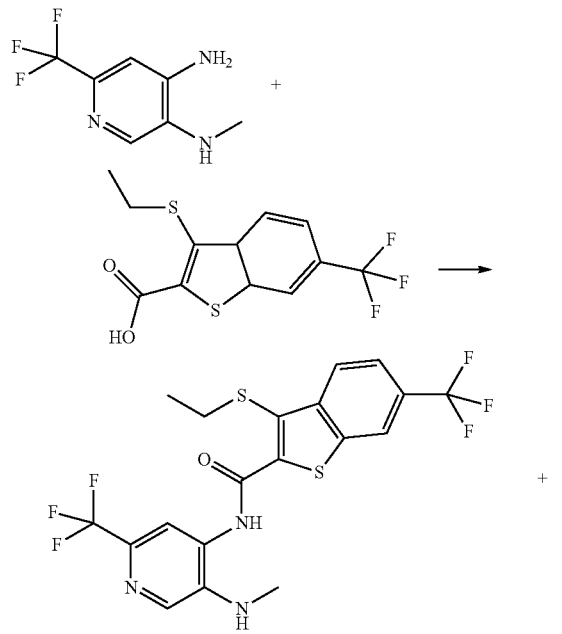

Prepared from N3-methyl-6-(trifluoromethyl)pyridine-3,4-diamine (Commercially available, Cas:1643139-91-6) and 3-ethylsulfanyl-6-(trifluoromethyl)benzothiophene-2-carboxylic acid (as described for the Example A5 (Step A), using a similar protocol as described in Example A3 (Step B). LC-MS (Method A) RT 1.11, 478 (MH−). 480 (MH+).

Step B: Synthesis of 2-[3-ethylsulfanyl-6-(trifluoromethyl)benzothiophen-2-yl]-3-methyl-6-(trifluoromethyl)imidazo[4,5-c]pyridine B3

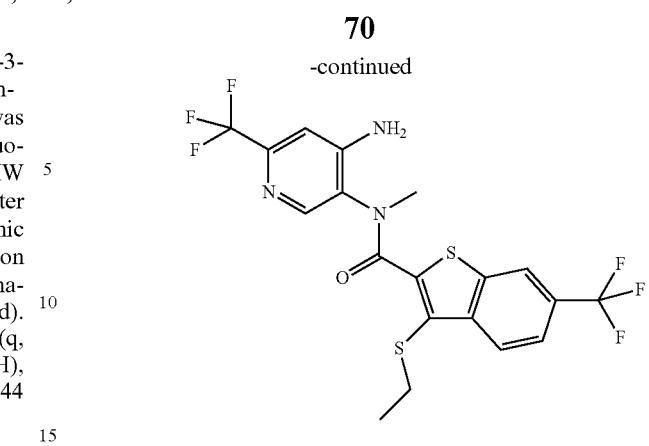

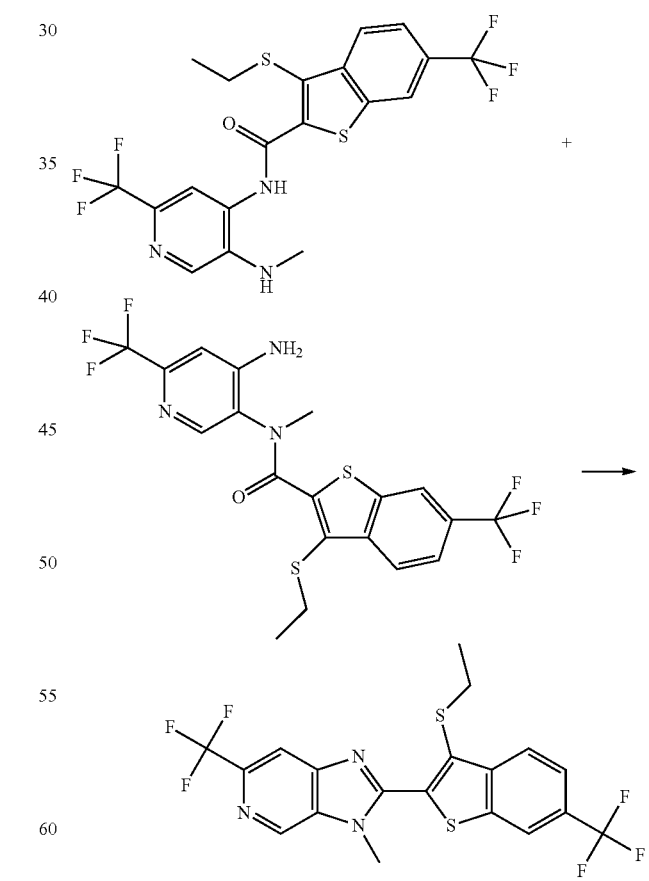

Prepared from 3-ethylsulfanyl-N-[5-(methylamino)-2-(trifluoromethyl)-4-pyridyl]-6-(trifluoromethyl)benzothiophene-2-carboxamide and N-[4-amino-6-(trifluoromethyl)-3-pyridyl]-3-ethylsulfanyl-N-methyl-6-(trifluoromethyl)

benzothiophene-2-carboxamide, using a similar protocol as described in Example A3 (step C). LC-MS (Method A) RT 1.23, 462 (MH+). $^1$H NMR (400 MHz, CDCl$_3$) δ ppm 1.03 (t, 3H), 2.67 (q, 2H), 3.98 (s, 3H), 7.80 (m, 1H), 8.18 (s, 1H), 8.26 (s, 2H), 9.01 (s, 1H).

Example B4: 2-[3-ethylsulfonyl-6-(trifluoromethyl) benzothiophen-2-yl]-3-methyl-6-(trifluoromethyl) imidazo[4,5-c]pyridine B4

B4

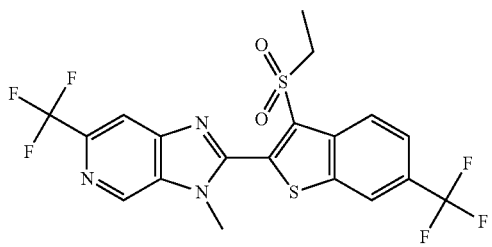

Prepared from 2-[3-ethylsulfanyl-6-(trifluoromethyl)benzothiophen-2-yl]-3-methyl-6-(trifluoromethyl)imidazo[4,5-c]pyridine B3, using a similar protocol as described in Example A4 Step A. LC-MS (Method A) RT 1.09, 492 (MH−), 494 (MH+). $^1$H NMR (400 MHz, CDCl$_3$) δ ppm 1.30 (t, 3H), 3.33 (q, 2H), 3.92 (s, 3H), 7.88 (dd, 1H), 8.15 (d, 1H), 8.31 (s, 1H), 8.69 (d, 1H), 9.01 (s, 1H).

Example B5: 2-(6-bromo-3-ethylsulfonyl-benzothiophen-2-yl)-3-methyl-6-(trifluoromethylsulfanyl)imidazo[4,5-c]pyridine B5

B5

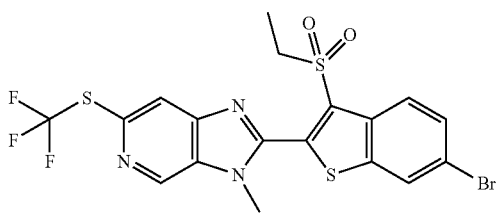

Step A: N-[4-amino-6-(trifluoromethylsulfanyl)-3-pyridyl]-6-bromo-3-ethylsulfanyl-N-methyl-benzothiophene-2-carboxamide and N-[4-amino-6-(trifluoromethylsulfanyl)-3-pyridyl]-6-bromo-3-ethylsulfanyl-N-methyl-benzothiophene-2-carboxamide

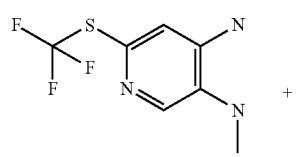 +

-continued

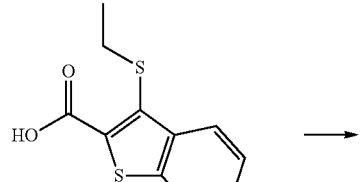

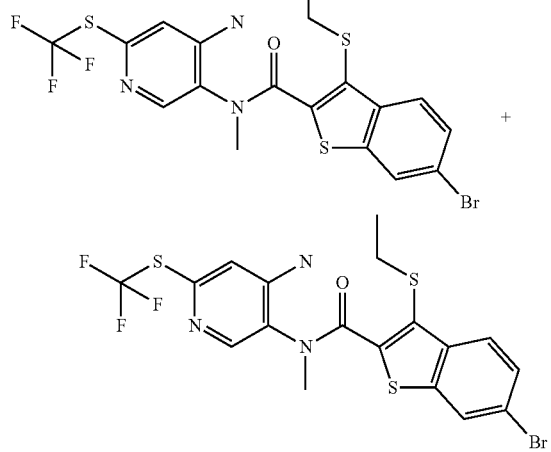

Prepared from N3-methyl-6-(trifluoromethylsulfanyl) pyridine-3,4-diamine (Commercially available, Cas: 1383840-73-0) and 6-bromo-3-ethylsulfanyl-benzothiophene-2-carboxylic acid (as described for the Example A3 step A) using a similar protocol as described in A3 Step B. LC-MS (Method A) RT 1.34, 522 (MH−) 524 (MH+).

Step B: 2-(6-bromo-3-ethylsulfanyl-benzothiophen-2-yl)-3-methyl-6-(trifluoromethylsulfanyl)imidazo [4,5-c]pyridine

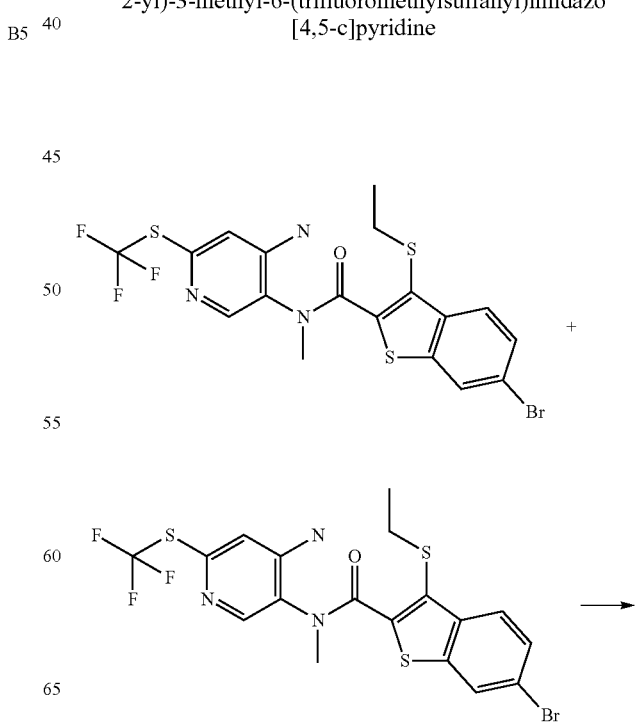

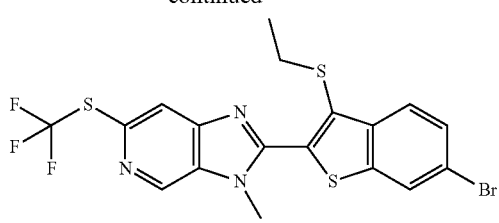

Prepared from N-[4-amino-6-(trifluoromethylsulfanyl)-3-pyridyl]-6-bromo-3-ethylsulfanyl-N-methyl-benzothiophene-2-carboxamide and N-[4-amino-6-(trifluoromethylsulfanyl)-3-pyridyl]-6-bromo-3-ethylsulfanyl-N-methyl-benzothiophene-2-carboxamide, using a similar protocol as described in Example A3 (step C). LC-MS (Method A) RT 1.30, 504 (MH+). ¹H NMR (400 MHz, CDCl₃) δ ppm 1.02 (t, 3H), 2.65 (q, 2H), 3.94 (s, 3H), 7.67 (dd, 1H), 7.98 (d, 1H), 8.10 (d, 1H), 8.17 (s, 1H), 8.95 (s, 1H).

Step C: 2-(6-bromo-3-ethylsulfonyl-benzothiophen-2-yl)-3-methyl-6-(trifluoromethylsulfanyl) imidazo[4,5-c] pyridine B5

B5

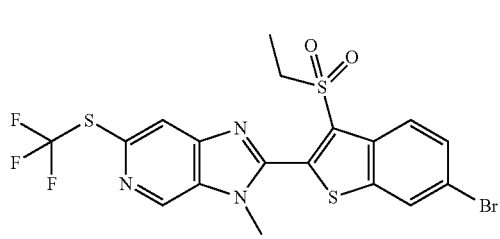

Prepared from 2-(6-bromo-3-ethylsulfanyl-benzothiophen-2-yl)-3-methyl-6-(trifluoromethylsulfanyl)imidazo[4,5-c]pyridine, using a similar protocol as described in Example A4 Step A (0.129 g; Yield=77%). LC-MS (Method A) RT 1.16, 538 (MH+). ¹H NMR (400 MHz, CDCL₃) δ ppm 1.28 (t, 3H), 3.30 (q, 2H), 3.88 (s, 3H), 7.76 (dd, 1H), 8.11-8.18 (m, 2H), 8.40 (d, 1H), 8.94 (s, 1H).

Example C1: 2-[3-ethylsulfonyl-6-(trifluoromethyl) benzothiophen-2-yl]-3-methyl-6-(trifluoromethyl) imidazo[4,5-c]pyridine C1

C1

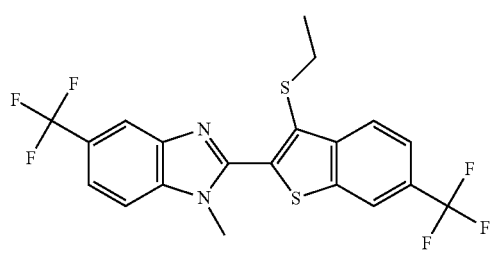

Step A: 3-ethylsulfanyl-N-[2-(methylamino)-5-(trifluoromethyl)phenyl]-6-(trifluoromethyl)benzothiophene-2-carboxamide and N-[2-amino-4-(trifluoromethyl)phenyl]-3-ethylsulfanyl-N-methyl-6-(trifluoromethyl)benzothiophene-2-carboxamide

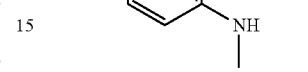

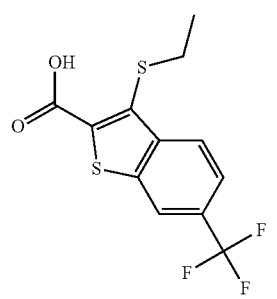

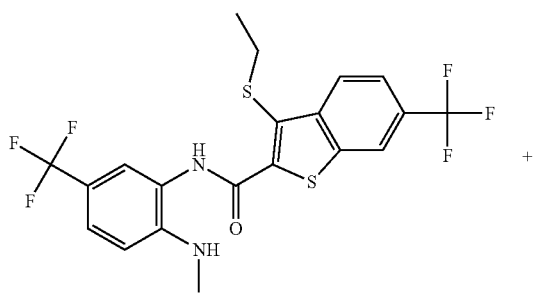

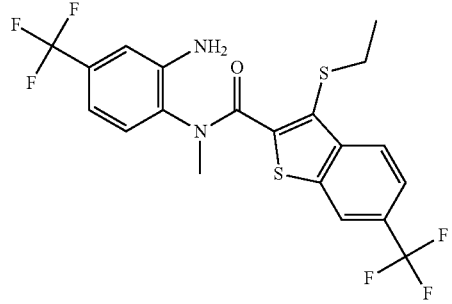

Prepared from intermediate N1-methyl-4-(trifluoromethyl)benzene-1,2-diamine (Commercially available CAS: 35203-49-7) and 3-ethylsulfanyl-6-(trifluoromethyl)benzothiophene-2-carboxylic acid (as described for the Example A5 Step A) using a similar protocol as described Example A3 Step B. LC-MS (Method A) RT 1.30, 477 (MH−) 479 (MH+).

Step B: 2-[3-ethylsulfanyl-6-(trifluoromethyl)benzothiophen-2-yl]-1-methyl-5-(trifluoromethyl)benzimidazole C1

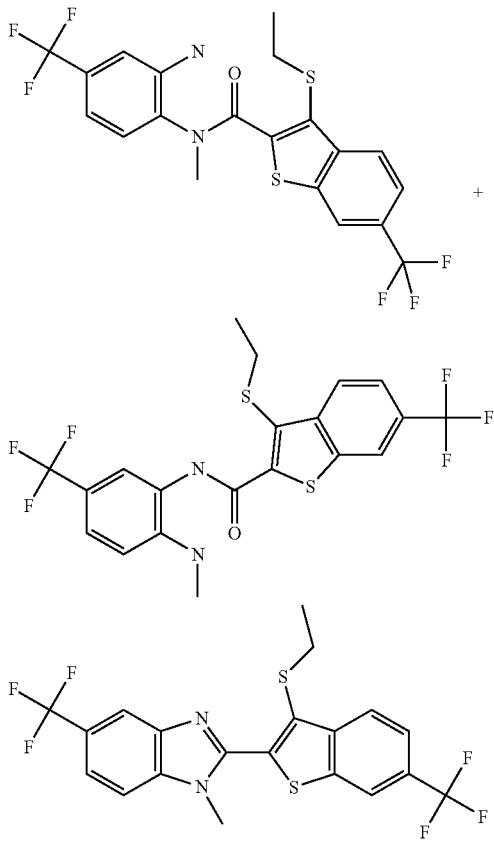

Prepared from 3-ethylsulfanyl-N-[2-(methylamino)-5-(trifluoromethyl)phenyl]-6-(trifluoromethyl)benzothiophene-2-carboxamide and N-[2-amino-4-(trifluoromethyl)phenyl]-3-ethylsulfanyl-N-methyl-6-(trifluoromethyl)benzothiophene-2-carboxamide, using a similar protocol as described in Example A3 (step C). LC-MS (Method A) RT 1.30, 460 (MH+). $^1$H NMR (400 MHz, CDCl$_3$) δ ppm 1.03 (t, 3H), 2.65 (q, 2H), 3.86 (s, 3H), 7.58 (m, 1H), 7.5 (m, 1H), 7.78 (m, 1H), 8.16 (s, 1H), 8.25 (m, 2H).

Example C2: 2-[3-ethylsulfonyl-6-(trifluoromethyl)benzothiophen-2-yl]-1-methyl-5-(trifluoromethyl)benzimidazole C2

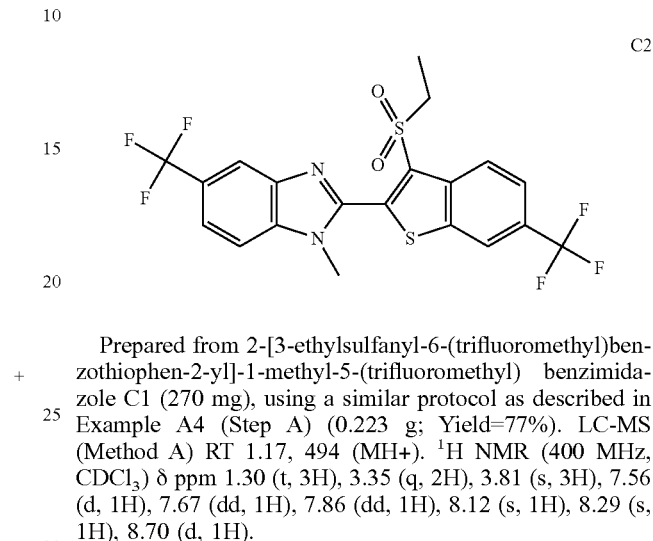

Prepared from 2-[3-ethylsulfanyl-6-(trifluoromethyl)benzothiophen-2-yl]-1-methyl-5-(trifluoromethyl) benzimidazole C1 (270 mg), using a similar protocol as described in Example A4 (Step A) (0.223 g; Yield=77%). LC-MS (Method A) RT 1.17, 494 (MH+). $^1$H NMR (400 MHz, CDCl$_3$) δ ppm 1.30 (t, 3H), 3.35 (q, 2H), 3.81 (s, 3H), 7.56 (d, 1H), 7.67 (dd, 1H), 7.86 (dd, 1H), 8.12 (s, 1H), 8.29 (s, 1H), 8.70 (d, 1H).

Table B discloses preferred compounds of the formula I-1a prepared according to the preparatory examples described above:

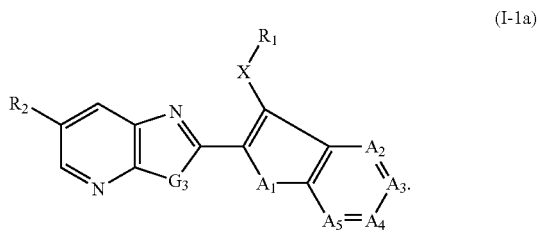

(I-1a)

TABLE B

| Comp. No. | X | R$_1$ | A$_1$ | R$_2$ | A$_2$ | A$_3$ | A$_4$ | A$_5$ | G$_3$ |
|---|---|---|---|---|---|---|---|---|---|
| A1 (1.001) | S | —CH$_2$CH$_3$ | S | CF$_3$ | CH | CH | CH | CH | N—CH$_3$ |
| A2 (1.002) | SO$_2$ | —CH$_2$CH$_3$ | S | CF$_3$ | CH | CH | CH | CH | N—CH$_3$ |
| A3 | S | —CH$_2$CH$_3$ | S | SCF$_3$ | CH | CH | CBr | CH | N—CH$_3$ |
| A4 | SO$_2$ | —CH$_2$CH$_3$ | S | SCF$_3$ | CH | CH | CBr | CH | N—CH$_3$ |
| A5 | S | —CH$_2$CH$_3$ | S | CF$_3$ | CH | CH | CCF$_3$ | CH | N—CH$_3$ |
| A6 | SO$_2$ | —CH$_2$CH$_3$ | S | CF$_3$ | CH | CH | CCF$_3$ | CH | N—CH$_3$ |
| A7 | S | —CH$_2$CH$_3$ | S | CF$_3$ | CH | CH | CBr | CH | N—CH$_3$ |
| A8 | SO$_2$ | —CH$_2$CH$_3$ | S | CF$_3$ | CH | CH | CBr | CH | N—CH$_3$ |
| A9 | SO$_2$ | —CH$_2$CH$_3$ | S | CF$_3$ | CH | CH | C(N-(3-(trifluoromethyl)-pyrazole)) | CH | N—CH$_3$ |
| A10 | SO$_2$ | —CH$_2$CH$_3$ | S | CF$_3$ | CH | CH | CSCF$_3$ | CH | N—CH$_3$ |
| A11 | SO$_2$ | —CH$_2$CH$_3$ | S | CF$_3$ | CH | CH | C$_3$H$_5$ | CH | N—CH$_3$ |
| A12 | SO$_2$ | —CH$_2$CH$_3$ | S | CF$_3$ | CH | CH | C$_2$F$_5$ | CH | N—CH$_3$ |

Table C discloses preferred compounds of the formula I-1b prepared according to the preparatory examples described above:

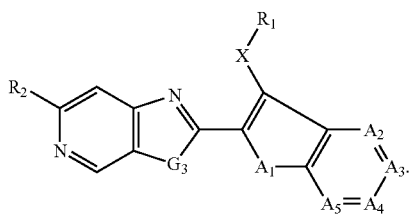

(I-1b)

TABLE C

| Comp. No. | X | $R_1$ | $A_1$ | $R_2$ | $A_2$ | $A_3$ | $A_4$ | $A_5$ | $G_3$ |
|---|---|---|---|---|---|---|---|---|---|
| B1 (2.001) | S | —$CH_2CH_3$ | S | $CF_3$ | CH | CH | CH | CH | N—$CH_3$ |
| B2 (2.002) | $SO_2$ | —$CH_2CH_3$ | S | $CF_3$ | CH | CH | CH | CH | N—$CH_3$ |
| B3 | S | —$CH_2CH_3$ | S | $CF_3$ | CH | CH | $CCF_3$ | CH | N—$CH_3$ |
| B4 | $SO_2$ | —$CH_2CH_3$ | S | $CF_3$ | CH | CH | $CCF_3$ | CH | N—$CH_3$ |
| B5 | $SO_2$ | —$CH_2CH_3$ | S | $SCF_3$ | CH | CH | CBr | CH | N—$CH_3$ |

Table D discloses preferred compounds of the formula I-1b prepared according to the preparatory examples described above:

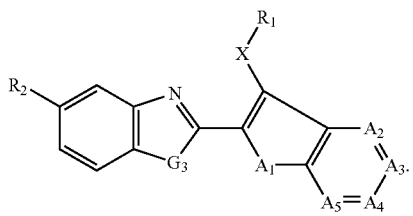

(I-1c)

TABLE D

| Comp. No. | X | $R_1$ | $A_1$ | $R_2$ | $A_2$ | $A_3$ | $A_4$ | $A_5$ | $G_3$ |
|---|---|---|---|---|---|---|---|---|---|
| C1 | S | —$CH_2CH_3$ | S | $CF_3$ | CH | CH | $CCF_3$ | CH | N—$CH_3$ |
| C2 | $SO_2$ | —$CH_2CH_3$ | S | $CF_3$ | CH | CH | $CCF_3$ | CH | N—$CH_3$ |

FORMULATION EXAMPLES (%=PERCENT BY WEIGHT)

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient | 80% | 10% | 5% | 95% |
| Ethyleneglycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | | |
|---|---|---|
| | a) | b) |
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | | | |
|---|---|---|---|
| | a) | b) | c) |
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

| Example F6: Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

| Example F7: Coated granules | |
|---|---|
| Active ingredient | 3% |
| Polyethyleneglycol (MW 200) | 3% |
| Kaolin | 94% |

In a mixer, the finely ground active ingredient is applied uniformly to the kaolin, which has been moistened with the polyethylene glycol. This gives dust-free coated granules.

| Example F8: Suspension concentrate | |
|---|---|
| Active ingredient | 40% |
| Ethyleneglycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

| Example F9: Powders for dry seed treatment | | | |
|---|---|---|---|
| | a) | b) | c) |
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Example F10: Emulsifiable concentrate | |
|---|---|
| active ingredient | 10% |
| octylphenol polyethyleneglycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Example F11: Flowable concentrate for seed treatment | |
|---|---|
| active ingredients | 40% |
| propyleneglycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 to 4 and A, B, C and D of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1 (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+

TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, niflurdide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nomicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, a molluscicide selected from the group of substances consisting of bis(tributyltin) oxide (IUPAC name) (913)+TX, bromoacetamide [CON]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol

[70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-d ihydroxy-4,6a,12b-trimethyl-11-oxo-9-(3-pyrid inyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Table 1 to 4 and A, B, C and D with active ingredients described above comprises a compound selected from Table 1 to 4 and A, B, C and D and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table 1 to 4 and A, B, C and D and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 to 4 and A, B, C and D and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

BIOLOGICAL EXAMPLES

Example B1: *Bemisia tabaci* (Cotton White Fly): Feeding/Contact Activity

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm:
A4, A6, A8, B4, B5 and C2.

Example B2: *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
A1, A2, A3, A4, A5, A6, A7, A8, A9, A10, A11, A12, B1, B2, B3, B4, B5, C1 and C2.

Example B3: *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A2, A3, A4, A5, A6, A7, A8, A10, A11, A12, B2, B3, B4 and B5.

Example B4: *Myzus persicae* (Green Peach Aphid): Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:
A1, A2, A4, A6, A8, A10, A11, B1, B2, B4 and B5.

Example B5: *Myzus persicae* (Green Peach Aphid): Intrinsic Activity

Test compounds prepared from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:
B1 and B3.

Example B6: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A2, A3, A4, A5, A6, A7, A8, A9, A10, A11, A12, B1, B2, B3, B4, B5, C1 and C2.

Example B7: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:
A2, A3, A4, A5, A6, A7, A8, A9, A10, A11, A12, B2, B3, B4, B5, C1 and C2.

Example B8: *Spodoptera littoralis* (Egyptian Cotton Leaf Worm)

Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:
A3, A4, A5, A6, A8, A10, B3, B4, B5 and C2.

Example B9: *Tetranychus urticae* (Two-Spotted Spider Mite): Feeding/Contact Activity Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
A3.

Example B10: *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h:
A3, A4, A5, A6, A7, A8, A10, A12, B3, B4, B5 and C2.

The invention claimed is:
1. A compound of formula I

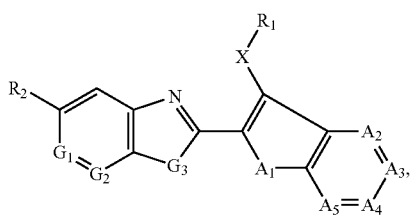

(I)

wherein
$A_1$ represents S, O or NCH$_3$;
$A_2$, $A_3$, $A_4$ and $A_5$, independently from each other, represent CR$_3$ or N;
X is S, SO or SO$_2$;
$R_1$ is C$_1$-C$_4$alkyl, C$_2$-C$_6$alkenyl, C$_2$-C$_6$haloalkenyl, C$_2$-C$_6$alkynyl, C$_1$-C$_4$haloalkyl, C$_3$-C$_6$cycloalkyl, C$_3$-C$_6$cycloalkyl-C$_1$-C$_4$alkyl; or is C$_3$-C$_6$cycloalkyl mono- or polysubstituted by substituents selected from the group consisting of halogen, cyano and C$_1$-C$_4$alkyl; or is C$_3$-C$_6$cycloalkyl-C$_1$-C$_4$alkyl mono- or polysubstituted by substituents selected from the group consisting of halogen, cyano and C$_1$-C$_4$alkyl;
$R_2$ is hydrogen, halogen, C$_1$-C$_4$haloalkylsulfanyl, C$_1$-C$_4$haloalkylsulfinyl, C$_1$-C$_4$haloalkylsulfonyl, O(C$_1$-C$_4$haloalkyl), —SF$_5$, —C(O)C$_1$-C$_4$haloalkyl, cyano, C$_1$-C$_6$haloalkyl or is C$_1$-C$_6$haloalkyl substituted by one or two substituents selected from the group consisting of hydroxyl, methoxy and cyano; or is C$_3$-C$_6$cycloalkyl which can be mono- or polysubstituted by substituents selected from the group consisting of halogen, cyano, C$_1$-C$_4$ haloalkyl and C$_1$-C$_4$alkyl;
$R_3$ is hydrogen, halogen, cyano, nitro, —SF$_5$, hydroxyl, amino, —NR$_9$R$_{10}$, C(O)NR$_9$R$_{10}$, C$_1$-C$_6$haloalkyl, C$_1$-C$_6$alkyl, C$_2$-C$_6$alkenyl, C$_2$-C$_6$alkynyl, C$_2$-C$_6$haloalkenyl, C$_2$-C$_6$haloalkynyl, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl, C$_1$-C$_4$alkylsulfonyl, O(C$_1$-C$_4$haloalkyl), —C(O)C$_1$-C$_4$haloalkyl, C$_1$-C$_6$haloalkoxy, C$_1$-C$_6$alkoxy, C$_2$-C$_4$alkylcarbonyl, C$_2$-C$_6$alkoxycarbonyl, C$_3$-C$_6$cycloalkyl which can be mono- or polysubstituted by R$_7$, or is C$_3$-C$_6$cycloalkyl-C$_1$-C$_4$alkyl which can be mono- or polysubstituted by R$_8$;

$R_3$ is pyrazolyl which can be mono- or polysubstituted by halogen, cyano or C$_1$-C$_6$haloalkyl
$G_1$ is CR$_4$;
$G_2$ is N;
$G_3$ is NR$_6$;
$R_6$ is C$_1$-C$_4$alkyl which can be mono- or polysubstituted by substituents selected from the group consisting of halogen and C$_1$-C$_2$alkylsulfinyl;
$R_4$ and $R_5$, independently from each other, are hydrogen, halogen, cyano, nitro, C$_1$-C$_6$alkyl, C$_1$-C$_6$haloalkyl, or are C$_3$-C$_6$cycloalkyl which can be mono- or polysubstituted by R$_7$; or are C$_3$-C$_6$cycloalkyl-C$_1$-C$_4$alkyl which can be mono- or polysubstituted by R$_8$; or
$R_4$ and $R_5$, independently from each other, are C$_2$-C$_6$alkenyl, C$_2$-C$_6$haloalkenyl, C$_2$-C$_6$alkynyl, C$_2$-C$_6$haloalkynyl, C$_1$-C$_6$haloalkoxy, C$_1$-C$_6$alkoxy, C$_1$-C$_6$alkylsulfanyl, C$_1$-C$_4$alkylsulfonyl, C$_1$-C$_6$alkylsulfinyl, C$_1$-C$_6$haloalkylsulfanyl, C$_1$-C$_4$haloalkylsulfonyl, C$_1$-C$_6$haloalkylsulfinyl or hydroxyl;
$R_7$ and $R_8$, independently from each other, are halogen, nitro, cyano, C$_1$-C$_4$haloalkoxy, C$_1$-C$_4$alkoxy C$_1$-C$_4$alkyl, C$_1$-C$_4$alkoxy, C$_1$-C$_4$alkyl or C$_1$-C$_4$haloalkyl;
$R_9$ and $R_{10}$, independently from each other, are hydrogen, cyano, C$_1$-C$_3$ alkoxy or C$_1$-C$_6$alkyl;

or an agrochemically acceptable salt, stereoisomer, enantiomer, tautomer or N-oxide thereof.

2. A compound of formula I according to claim 1 represented by the compounds of formula I-1a

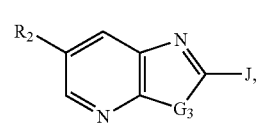

(I-1a)

wherein J is selected from the group consisting of

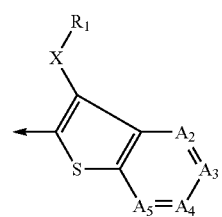

J1

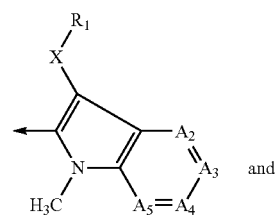

J2 and

-continued

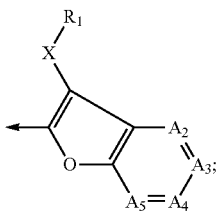

J3 wherein
R₁ is $C_1$-$C_4$alkyl, $C_3$-$C_6$cycloalkyl-$C_1$-$C_4$alkyl or $C_3$-$C_6$cycloalkyl;
R₂ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl; and
$G_3$, X, $A_2$, $A_3$, $A_4$ and $A_5$ are as defined under formula I in claim 1.

3. A compound of formula I represented by the formula I-1a

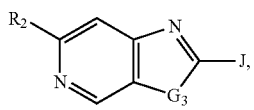
(I-2a)

wherein J is as defined as

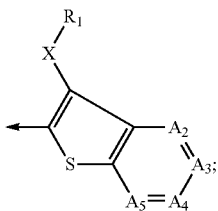
J1

$R_2$ is $C_1$-$C_2$ haloakyl, $C_1$-$C_2$haloalkylsulfanyl, $C_1$-$C_2$haloalkylsulfinyl or $C_1$-$C_2$ haloalkylsulfonyl;
$G_3$ is N—$R_6$, wherein $R_6$ is $C_1$-$C_2$alkyl;
$A_2$, $A_3$, $A_4$ and $A_5$, independently from each other, are $CR_3$ or N, wherein $R_3$ is $C_1$-$C_4$ haloalkyl, hydrogen, halogen, cyclopropyl or pyrazolyl, or cyclopropyl or pyrazolyl which can be substituted by $C_1$-$C_2$haloakyl.

4. An arthropodal pesticidal composition, which comprises at least one compound of formula I according to claim 1 or, where appropriate, a tautomer thereof, in each case in free form or in agrochemically utilizable salt form, as active ingredient and at least one auxiliary.

5. A method for controlling arthropodal pests, which comprises applying a composition according to claim 4 to the pests or their environment with the exception of a method for treatment of the human or animal body by surgery or therapy and diagnostic methods practiced on the human or animal body.

6. A method for the protection of seeds from the attack by arthropodal pests, which comprises treating the seeds or the site, where the seeds are planted, with a composition according to claim 4.

7. The arthropodal pesticidal composition of claim 4, wherein the arthropod is an insect.

8. The arthropodal pesticidal composition of claim 4, wherein the arthropod is an acarina.

9. The method for controlling arthropodal pests of claim 5, wherein the arthropod is an insect.

10. The method for controlling arthropodal pests of claim 5, wherein the arthropod is an acarina.

11. The method for the protection of seeds from the attack by arthropodal pests of claim 6, wherein the arthropod is an insect.

12. The method for the protection of seeds from the attack by arthropodal pests of claim 6, wherein the arthropod is an acarina.

* * * * *